US007132247B1

(12) United States Patent
Lyngberg et al.

(10) Patent No.: US 7,132,247 B1
(45) Date of Patent: Nov. 7, 2006

(54) COMPOSITE DEVICES INCORPORATING BIOLOGICAL MATERIAL AND METHODS

(75) Inventors: Olav K. Lyngberg, Princeton Junction, NJ (US); Michael C. Flickinger, St. Anthony Park, MN (US); L. Edward Scriven, II, Minneapolis, MN (US); Ron Anderson, Apple Valley, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 09/647,475

(22) PCT Filed: Sep. 17, 1999

(86) PCT No.: PCT/US99/21581

§ 371 (c)(1),
(2), (4) Date: Aug. 20, 2001

(87) PCT Pub. No.: WO00/16098

PCT Pub. Date: Mar. 23, 2000

Related U.S. Application Data

(60) Provisional application No. 60/100,914, filed on Sep. 17, 1998.

(51) Int. Cl.
*G01N 33/53* (2006.01)

(52) U.S. Cl. .................. 435/7.2; 435/7.21; 435/7.6; 435/7.92; 435/7.5; 422/105; 422/119

(58) Field of Classification Search ............... 435/6, 435/7.4, 7.6, 7.92, 7.95, 7.2; 422/105, 119
See application file for complete search history.

(56) References Cited

U.S. PATENT DOCUMENTS

| 3,992,158 | A |   | 11/1976 | Przybylowicz et al. |
|-----------|---|---|---------|---------------------|
| 4,050,898 | A |   | 9/1977  | Goffe et al. |
| 4,444,879 | A | * | 4/1984  | Foster et al. ............... 435/7.95 |
| 4,797,363 | A |   | 1/1989  | Teodorescu et al. |
| 5,026,641 | A | * | 6/1991  | Ishizaki ....................... 435/101 |
| 5,447,836 | A |   | 9/1995  | Wolber et al. |
| 5,498,525 | A |   | 3/1996  | Rees et al. |
| 5,571,722 | A |   | 11/1996 | Rosson |
| 5,612,184 | A |   | 3/1997  | Rosson |
| 5,723,330 | A |   | 3/1998  | Rees et al. |
| 5,728,350 | A |   | 3/1998  | Kinoshita et al. |
| 5,751,629 | A | * | 5/1998  | Nova et al. .................. 365/151 |
| 5,763,170 | A |   | 6/1998  | Raybuck |
| 5,776,681 | A |   | 7/1998  | Virta et al. |
| 5,804,083 | A |   | 9/1998  | Ishii et al. |
| 5,855,836 | A |   | 1/1999  | Leyden et al. |
| 5,879,951 | A |   | 3/1999  | Sy |
| 5,925,511 | A |   | 7/1999  | Fuhr et al. |
| 5,927,547 | A |   | 7/1999  | Papen et al. |
| 6,079,283 | A |   | 6/2000  | Papen et al. |
| 6,083,762 | A |   | 7/2000  | Papen et al. |
| 6,094,966 | A |   | 8/2000  | Papen et al. |
| 6,475,808 | B1| * | 11/2002 | Wagner et al. ............... 436/518 |
| 2001/0041339 | A1 | * | 11/2001 | Anderson et al. ............... 435/6 |

FOREIGN PATENT DOCUMENTS

| EP | 0 168 933 A2 | 1/1986 |
|----|--------------|--------|
| EP | 0 318 452 A1 | 5/1989 |
| EP | 0 469 021 B1 | 2/1992 |
| EP | 0 711 199 B1 | 5/1996 |
| GB | 0288203      | * 10/1988 |
| JP | 62138502     | 6/1987 |
| JP | 62294083     | 12/1987 |
| JP | 0314338      | * 3/1989 |
| WO | WO 89/03878  | 5/1989 |
| WO | WO 90/04037  | 4/1990 |
| WO | WO 90/04041  | 4/1990 |
| WO | WO 90/05910  | 5/1990 |
| WO | WO 90/08836  | 8/1990 |
| WO | WO 90/12887  | 11/1990 |
| WO | WO 92/15687  | 9/1992 |
| WO | WO 95/03878  | 2/1995 |
| WO | WO 95/19446  | 7/1995 |
| WO | WO 95/25116  | 9/1995 |
| WO | WO 96/13159  | 5/1996 |
| WO | WO 00/16098  | 3/2000 |

OTHER PUBLICATIONS

Lyngberg et al. A single-use luciferase-based mercury biosensor using *E coli* HB 101 immobilized in a latex copolmyer film J. Ind. Microbiol. Biotech. (1999) 23: 668-676.*
Mulchandani et al. Analytical Chem. 1998 70: 4140.*
Martens et al. (Analytica Chimica Acta 1994 vol. 292: 49-63).*
Hart et al., "On the use of screen- and ink-jet printing to produce amperometric enzyme electrodes for lactate," *Biosensors and Bioelectronics*, 1996;11(3):263-270.
Hart et al., "Recent developments in the design and application of screen-printed electrochemical sensors for biomedical, environmental and industrial analyses," *Trends in Analytical Chemistry*, 1997;16(2):89-103.
Dow Reichhold Specialty Latex LLC, Material Safety Data Sheet, Material Description: Latex DL 233NA, Effective Date: Jan. 3, 2006, MSDS No. DRSL0001, Material Code: 150984, Research Triangle Park, NC, 7 pgs.
Dow Reichhold Specialty Latex LLC, Product Bulletin, DL 233, 1 pg.
Flickinger, Michael C., Biotechnology Development grant (no abstract on file), Grant No. 1T32GM08347-01A1 [online]. National Institutes of General Medical Sciences, project dates Sep. 25, 1990-Jun. 30, 1995 [retrieved on Jan. 24, 2001]. Retrieved from the Internet: URL: http.commons.cit.nih.gov/crisp_historical/crisp_lib.getdoc?textkey=3538536&p_grant_num=1T32GM08347-01A1&p_query=ticket=18343&p_audit_session_id=334651&p_keywords=>, 1 page.

(Continued)

*Primary Examiner*—Long V. Le
*Assistant Examiner*—Jacob Cheu
(74) *Attorney, Agent, or Firm*—Mueting, Raasch & Gebhardt, P.A.

(57) ABSTRACT

The present invention provides composite biological devices that include biological material as an integral component thereof. The devices can be used for measuring metals, for example, particularly toxic metals such as mercury.

39 Claims, 16 Drawing Sheets

OTHER PUBLICATIONS

Flickinger, Michael C., Biotechnology Development grant (no abstract on file), Grant No. 5T32GM08347-02 [online]. National Institutes of General Medical Sciences, project dates Sep. 25, 1990-Jun. 30, 1995 [retrieved on Jan. 24, 2001]. Retrieved from the Internet: URL: http.commons.cit.nih.gov/crisp_historical/crisp_lib.getdoc?textkey=3538537&p_grant_num=5T32GM08347-02&p_query=ticket=18343&p_audit_session_id=334651&p_keywords=>, 1 page.

Flickinger, Michael C., Biotechnology Development grant (no abstract on file), Grant No. 5T32GM08347-03 [online]. National Institutes of General Medical Sciences, project dates Sep. 25, 1990-Jun. 30, 1995 [retrieved on Jan. 24, 2001]. Retrieved from the Internet: URL: http.commons.cit.nih.gov/crisp_historical/crisp_lib.getdoc?textkey=3538538&p_grant_num=5T32GM08347-03&p_query=ticket=18343&p_audit_session_id=334651&p_keywords=>, 1 page.

Flickinger, Michael C., Biotechnology Development grant (no abstract on file), Grant No. 5T32GM08347-04 [online]. National Institutes of General Medical Sciences, project dates Sep. 25, 1990-Jun. 30, 1995 [retrieved on Jan. 24, 2001]. Retrieved from the Internet: URL: http.commons.cit.nih.gov/crisp_historical/crisp_lib.getdoc?textkey=2167984&p_grant_num=5T32GM08347-04&p_query=ticket=18343&p_audit_session_id=334651&p_keywords=>, 1 page.

Flickinger, Michael C., Biotechnology Development grant (no abstract on file), Grant No. 5T32GM08347-05 [online]. National Institutes of General Medical Sciences, project dates Sep. 25, 1990-Jun. 30, 1995 [retrieved on Jan. 24, 2001]. Retrieved from the Internet: URL: http.commons.cit.nih.gov/crisp_historical/crisp_lib.getdoc?textkey=2167985&p_grant_num=5T32GM08347-05&p_query=ticket=18343&p_audit_session_id=334651&p_keywords=>, 1 page.

Flickinger, Michael C. "Enhanced Gene Expression in Immobilized Whole-Cell Biocatalysis," Grant No. 9424063, Continuing Grant, Aug. 1, 1995-Jul. 31, 1998 (abstract) [online]. National Science Foundation, Division of Bioengineering and Environmental Systems, Washington, D.C. [retrieved Jan. 23, 2001]. Retrieved from: Dialog Information Services, FEDRIP Database, 1 page.

Freemantle, "Downsizing Chemistry: Chemical analysis and synthesis on microchips promise a variety of potential benefits," *Chemical and Engineering News*, 77(8):27-36 (Feb. 22, 1999).

Hellemans, "Rubber Mold Carves a Path to Micromachines," *Science*, 285(5424):19, 21 (Jul. 2, 1999).

Huang et al., "Microstructure Evolution in Polymer Latex Coatings for Whole-Cell Biocatalyst Application," *Journal of Colloid and Interface Science*, 215(2):226-243 (Jul. 15, 1999).

Kenis et al., "Microfabrication Inside Capillaries Using Multiphase Laminar Flow Patterning," *Science*, 285(5424):83-85 (Jul. 2, 1999).

Lyngberg, "Patch Coating a Bio-indicator," Abstract and Poster, Coating Process Fundamentals Program—Fall Review, University of Minnesota Center for Interfacial Engineering, NSF Engineering Research Center, 17 pages (Sep. 22, 1997; Web publication Sep. 17, 1997).

Lyngberg et al., "Mercury Detection Using Latex Immobilized Cells," Abstract and Poster, Meeting, North Central Branch American Society of Microbiology, St. Cloud State University, MN, 10 pages (Oct. 1997).

Lyngberg et al., "A single-use luciferase-based biosensor using copolymer-film immobilized viable *E. coli* HB101,"Abstract, database CHEMABS [Online] Chemical Abstracts Service, Columbus, Ohio, retrieved from STN XP002127579 & Book of Abstracts, 216th ACS National Meeting, Boston, Aug. 23-27, (1998).

Lyngberg et al., "A Patch Coating Method for Preparing Biocatalytic Films of *Escherichia coli*," *Biotechnology and Bioengineering*, 62(1):44-55 (Jan. 5, 1999).

Lyngberg et al., "A single-use luciferase-based mercury biosensor using *Escherichia coli* HB101 immobilized in a latex copolymer film,"Abstract, CHEMABS [Online] Chemical Abstracts Service, Columbus, Ohio, retrieved from STN database accession No. 131:268025 XP002127580 & *Journal of Industrial Microbiology and Biotechnology*, 23(1):668-676 (1999).

Lyngberg et al., "A single-use luciferase-based mercury biosensor using *Escherichia coli* HB101 immobilized in a latex copolymer film," *Journal of Industrial Microbiology and Biotechnology*, 23(1):668-676 (Jul. 1999).

Maniatis et al., *Molecular Cloning: A Laboratory Manual*, Cold Spring Harbor Laboratory Press, Cold Spring Harbor, New York, Title page, publication page and table of contents only, 8 pages (1982).

Martens et al., "Immobilisation of photosynthetic cells based on film-forming emulsion polymers," *Analytica Chimica Acta*, 292:49-63 (1994).

Selifonova et al., "Bioluminescent Sensors for Detection of Bioavailable Hg(II) in the Environment," *Applied and Environmental Microbiology*, 59(9):3083-3090 (1993).

Swope et al., "Activation and Regeneration of Whole Cell Biocatalysts: Initial and Periodic Induction Behavior in Starved *Escherichia coli* after Immobilization in Thin Synthetic Films," *Biotechnology and Bioengineering*, 51:360-370 (1996).

Swope et al., "The Use of Confocal Scanning Laser Microscopy and Other Tools to Characterize *Escherichia coli* in a High-Cell-Density Synthetic Biofilm," *Biotechnology and Bioengineering*, 52:340-356 (1996).

Swope et al., "Investigation of Gene Expression in Synthetic Biofilms to Extend the Activity of Immobilized Whole Cell Catalysts," *Progress in Biotechnology 11, Immobilized Cells: Basics and Applications*, Proceedings of an International Symposium, The Working Party on Applied Biocatalysis of the European Federation of Biotechnology, The Netherlands, pp. 313-319 (Nov. 26-29, 1995).

Thiagarajan et al., "Cryo-Electron Microscopy of Polymer Particles in a High Cell Density Synthetic Biofilm," *Progress in Biotechnology 11, Immobilized Cells: Basics and Applications*, Proceedings of an International Symposium, The Working Party on Applied Biocatalysis of the European Federation of Biotechnology, The Netherlands, pp. 298-303 (Nov. 26-29, 1995).

Thiagarajan et al., "Investigation of Oxygen Consumption by *E. coli* Immobilized in a Synthetic Biofilm Using a Thin Film Plug Reactor (TFPR)," *Progress in Biotechnology 11, Immobilized Cells: Basics and Applications*, Proceedings of an International Symposium, The Working Party on Applied Biocatalysis of the European Federation of Biotechnology, The Netherlands, pp. 304-312 (Nov. 26-29, 1995).

Thiagarajan et al., "Microstructure of a Biocatalytic Latex Coating Containing Viable *Escherichia coli* Cells," *Journal of Colloid and Interface Science*, 215(2):244-257 (Jul. 15, 1999).

\* cited by examiner

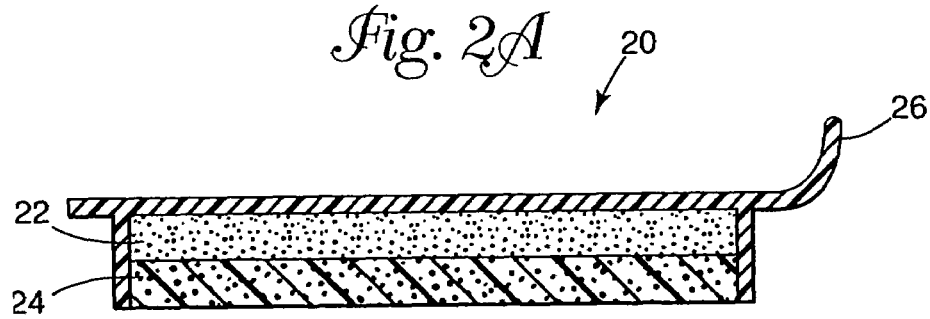
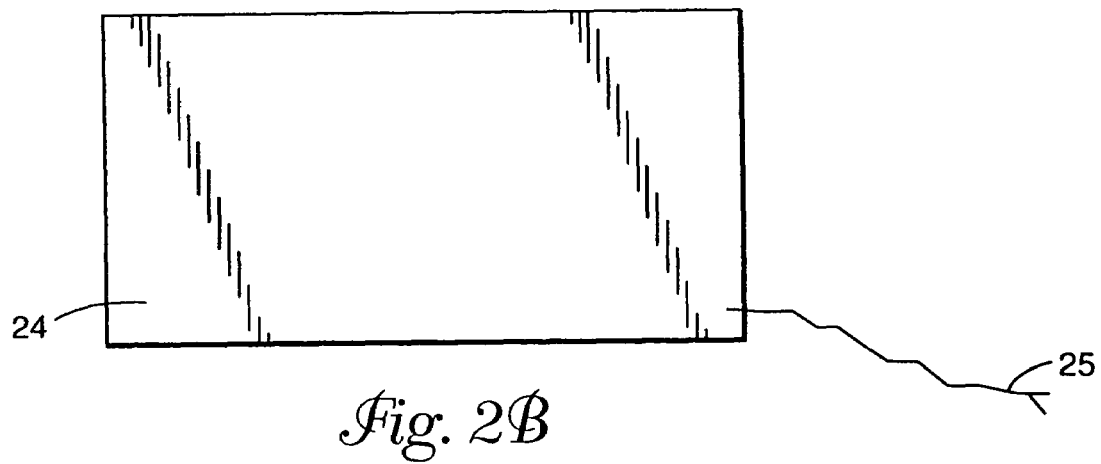

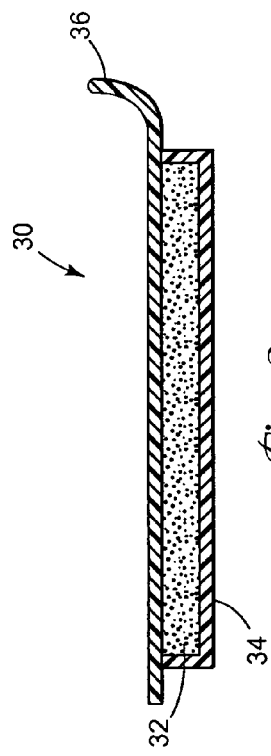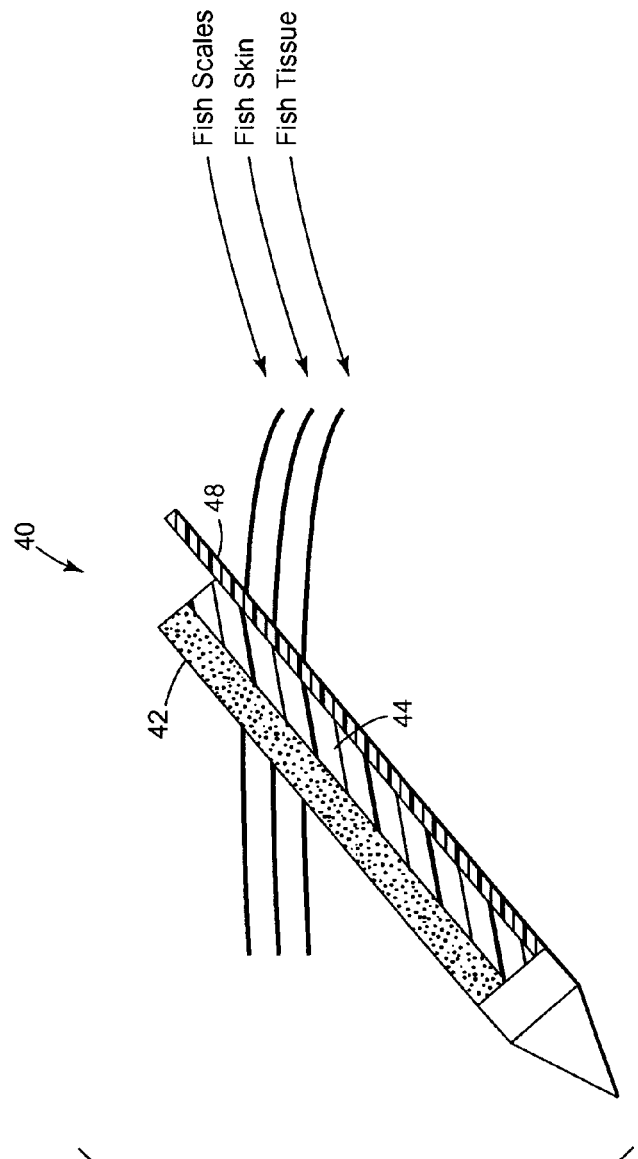

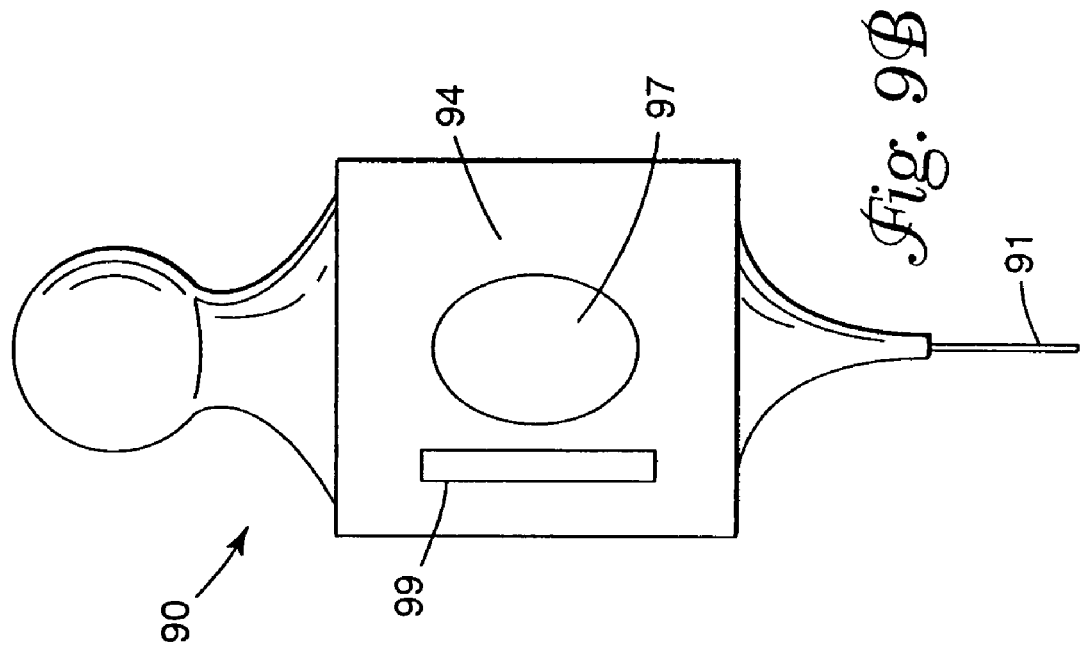
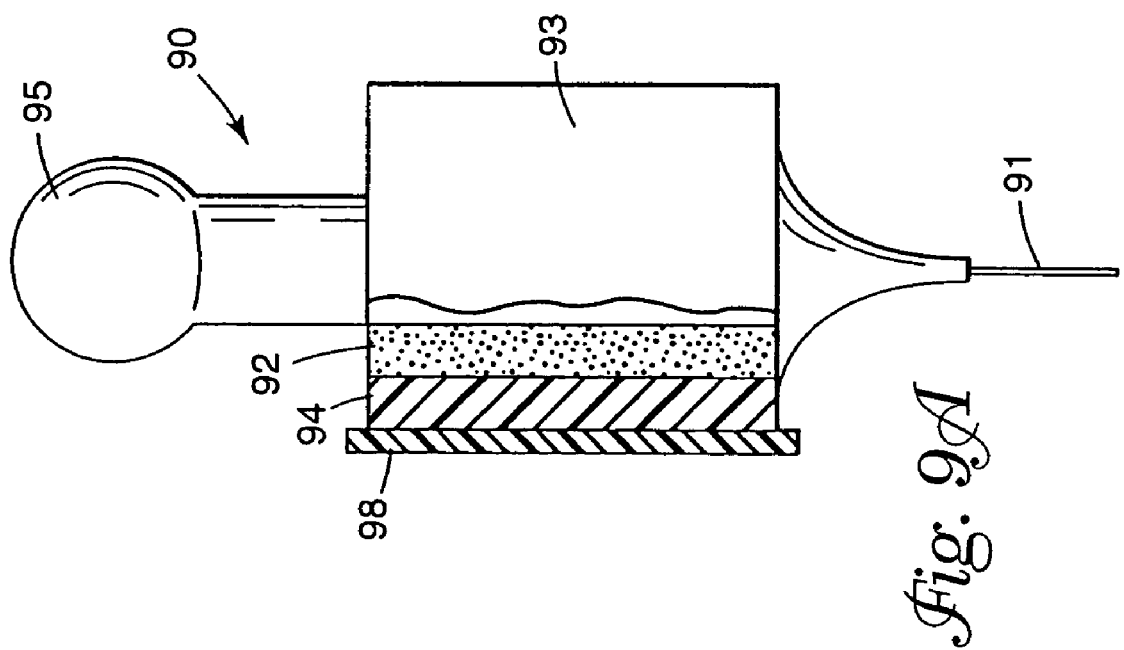

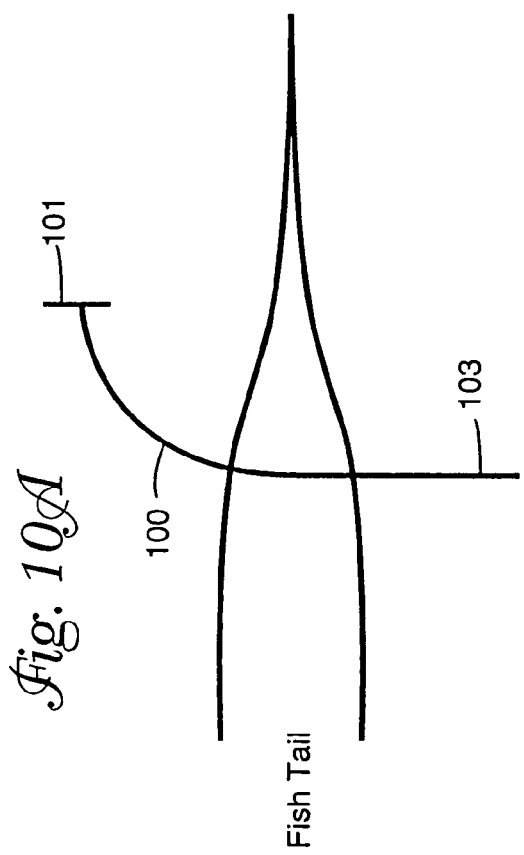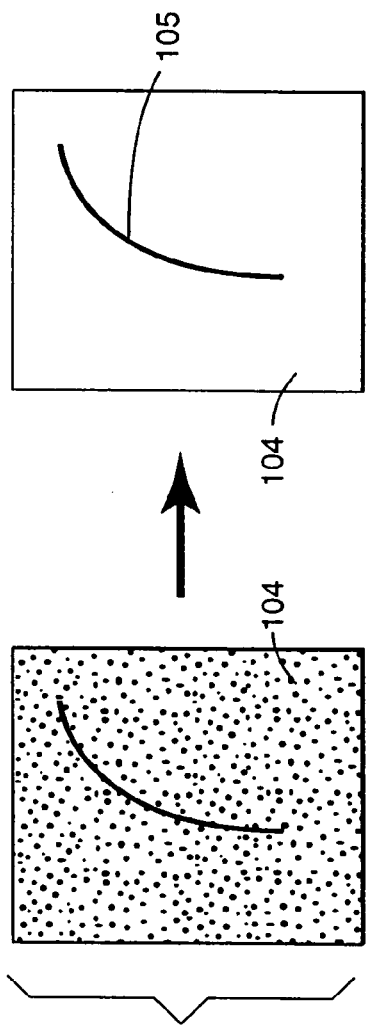

Fig. 11A
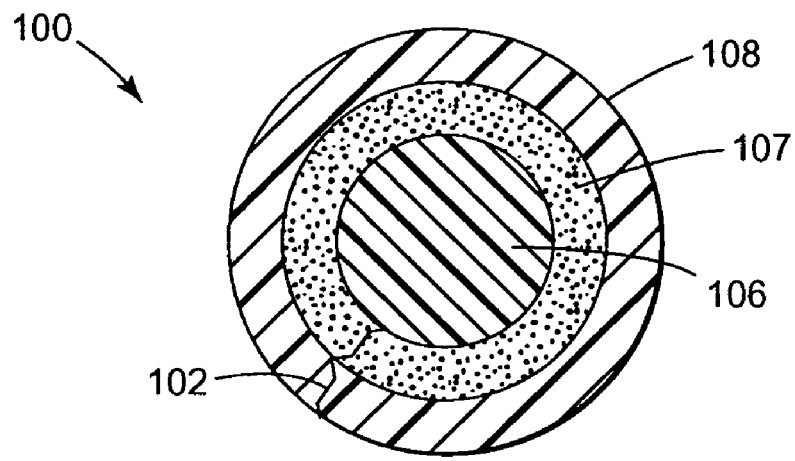
Coating on a Mono-filament
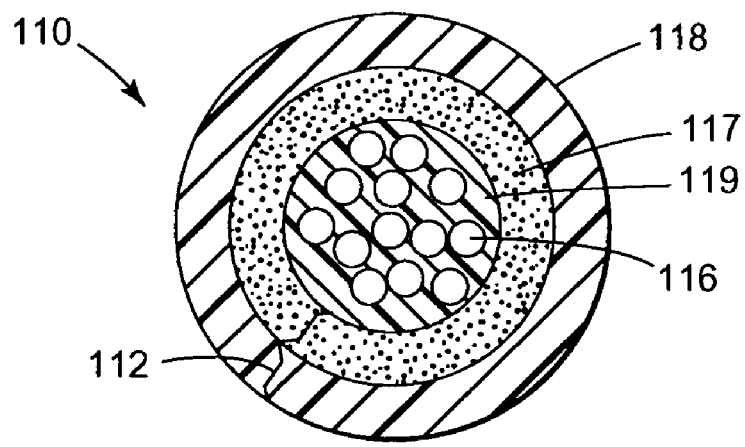
Coating on a Thread
Containing Multiple Filaments
Fig. 11B

COMPOSITE DEVICES INCORPORATING BIOLOGICAL MATERIAL AND METHODS This application is a U.S. National Stage Application which claims priority to International Application No. PCT/US99/21581, filed Sep. 17, 1999, and also claims priority to U.S. Provisional Application No. 60/100,914, filed Sep. 17, 1998, which are incorporated herein by reference.

STATEMENT OF GOVERNMENT RIGHTS

The present invention was made with support of the National Science Foundation under Grant No. 9424063. The government may have certain rights in this invention.

FIELD OF THE INVENTION

The present inventions provides composite devices that include biological material as an integral element, as well as methods of their use and preparation. Such devices can be used for screening drugs, chemical catalysis, implanting (into mammals, birds, fish), bioelectronic applications, biosensor applications (including single use indictors and sensors that can be released into the environment). An example of this concept is a device for measuring environmental contaminants such as metals.

BACKGROUND OF THE INVENTION

Metabolically active biological materials (e.g., cells) are phenomenal biochemical catalysts capable of carrying out sequential, stereospecific biochemical reactions, and can function as sensitive biosensors. There are significant potential industrial, biomedical, and environmental uses of metabolically active biological materials. They can be used for a variety of purposes such as detecting and/or measuring the amount of an environmental contaminant, particularly metals.

Metal contamination, particularly mercury, arsenic, cadmium, chromium, and nickel contamination, continues to be a public health and environmental problem. Conventional chemical detection techniques include atomic absorption spectrophotometery, ion chromatography, gas chromatography, mass spectrometry, as well as cold-vapor atomic absorption or cold-vapor atomic fluorescence spectroscopy. At least some of these techniques can be highly sensitive but complex to perform and expensive in terms of equipment and training. Furthermore, these techniques must typically be conducted in the laboratory. Plus, these techniques do not always reflect the true biological availability of toxic metals in a system.

Microorganisms that quantitatively detect toxins in the environment offer a less expensive alternative to conventional methods. For example, microbial biosensors aimed at measuring the bioavailability of mercury have been developed as an alternative to chemical or physical analysis. U.S. Pat. No. 5,612,184 (Rosson) discloses a device for the detection of mercury in water using an aqueous suspension of recombinant biosensory microorganism cells containing a lux bioluminescence gene. The cells are bioluminescent in the presence of $Hg^{2+}$ ions and/or monomethyl mercury. The resultant bioluminescence can be detected using a variety of means, e.g., photographic film, photomultiplier, photodiode, or scintillation counter. However, this patent only discloses the use of such a suspended cell biosensor for the detection of mercury in water. Furthermore, suspended cell biosensors are limited because of handling difficulties and short useful life of the cell stock solution.

Immobilization of cells for the biodetection of contaminants in aqueous environments offers advantages over the use of suspended cell systems. Immobilized cells are easy to handle, can remain viable for long periods of time, and show excellent plasmid retention. However, immobilization methods for use in biosensors have focused on reusable detection methods where the immobilized cells are used repeatedly. In such methods, control over immobilized cell stability and cell outgrowth become considerable problems together with slow biosensor response times.

SUMMARY OF THE INVENTION

The present invention is directed to composite devices that incorporate one or more biological materials (e.g., microorganism such as prokaryotic, eukaryotic, or archean organisms, as well as mammalian cells, blood cells, avian cells, plant cells, insect cells, spores, phages, viruses, etc.) as an integral element. The biological material is preferably viable, i.e., metabolically active, and substantially permanently immobilized within the devices. The present invention significantly expands on the potential industrial, biomedical, and environmental uses of metabolically active biological materials (such as cells) by incorporating them as an integral component of composite devices. For example, these devices can be used for a variety of purposes such as detecting and/or measuring the amount of an environmental contaminant, drug, organic or inorganic compound that indicates the quality or purity of air, water, soil, or foods.

In one embodiment, the present invention provides a composite biological device. The device includes a biostructure that includes at least one metabolically active biological material as an integral component thereof. At least a portion of the biostructure includes a nonporous latex-derived material. Preferably, the biostructure includes at least one layer of a porous latex-derived material and at least one layer of a nonporous latex-derived material. The nonporous material can be used to create a variety of structures within the device. For example, nonporous material can define at least one channel or at least one well.

The biostructures of the devices of the present invention may be self supporting or may be disposed on a substrate. Preferably, the biostructures are very thin. For example, they are preferably, no greater than about 500 microns in thickness, more preferably, no greater than about 100 microns in thickness, and most preferably, no greater than about 10 microns. For certain embodiments, the entire device is no greater than about 500 microns in thickness.

In another embodiment, the present invention provides a composite biological device that includes a 3-dimensional porous latex-derived biostructure having at least one metabolically active biological material incorporated therein; wherein the biostructure is disposed on a porous substrate.

In yet another embodiment, the present invention provides a composite biological device that includes a 3-dimensional porous latex-derived biostructure having at least one metabolically active biological material incorporated therein; wherein the porous latex-derived biostructure contains at least two portions of different pore size.

The present invention also provides a method of making a composite biological device. The method includes depositing at least one latex in a first layer; depositing at least one latex in a second layer on the first layer to form a microstructure; depositing at least one metabolically active biological material separately or in a combination with at least one latex such that the biological material is incorporated into the microstructure; wherein at least one of the latices forms a nonporous component of the microstructure. The method preferably involves ink-jet printing with an ink-jet printer.

In a preferred embodiment, the present invention provides a composite biological device for determining the presence of a metal in a sample. The composite biological device includes a biostructure having at least one biological material which, upon contact with the metal, produces a response and emits a signal. Preferably, the biological material includes bacterial cells immobilized (preferably, permanently entrapped) in one or more layers of a polymeric material. Preferably, the cells are genetically engineered to produce a response, such as luminescence, to the metal of interest. In certain embodiments, the biostructure is disposed on a substrate that is capable of detecting the signal. In such embodiments, the substrate is a photosensitive film or a light-sensitive electronic chip, for example.

The present invention also provides a method of determining the presence of an analyte (e.g., metal) in a sample (e.g., liquid, gas, solid, or semi-solid sample). The method comprises contacting the sample with a device as described herein, wherein, upon contact with the analyte, the biological material produces a response and emits a signal; and detecting the signal.

BRIEF DESCRIPTION OF THE DRAWINGS

FIG. 2A is a cross-sectional schematic of an alternative embodiment of a device according to the present invention using a light-sensitive electronic chip as the supporting substrate.

FIG. 2B is a bottom view of the device of FIG. 2A showing the light-sensitive electronic chip.

FIG. 3 is a cross-sectional schematic of an alternative embodiment of a device according to the present invention using a solid light-proof or light impenetrable backing as the supporting substrate.

FIG. 4 is a cross-sectional schematic of an alternative embodiment of a device according to the present invention that is used to penetrate a solid sample such as fish tissue.

FIG. 9A is a cross-sectional schematic of an alternative embodiment of a device according to the present invention that incorporates a photosensitive film as the supporting substrate and isolates the person taking the sample from the sampled material, thereby preventing the transfer of disease.

FIG. 9B is a side view of the device of FIG. 9A showing the photosensitive film.

FIG. 10A is a cross-sectional schematic of an alternative embodiment of a device according to the present invention that uses a coated fiber in which the coating contains immobilized cells.

FIG. 10B shows an incubation pouch containing a photosensitive film used for detecting a signal emitted by the cells of the coated fiber of FIG. 10A.

FIG. 11A is a cross-section of a monofilament coated with immobilized cells.

FIG. 11B is a cross-section of a multiple filament thread coated with immobilized cells.

DETAILED DESCRIPTION OF PREFERRED EMBODIMENTS

Figure 1A:
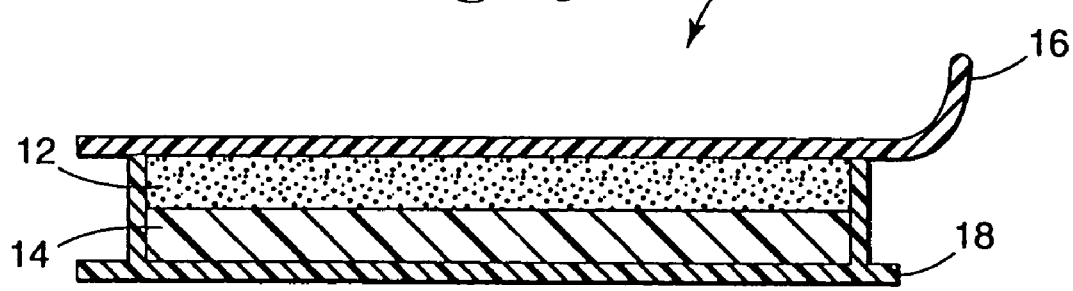
FIG. 1A is a cross-sectional schematic of one embodiment of a device according to the present invention using a photosensitive film as the supporting substrate.

The present invention provides devices that include as an integral component thereof biological material, preferably, metabolically active biological material. By incorporating metabolically active biological material (e.g., cells) as an integral component, the composite biological devices of the present invention expand on the potential industrial, biomedical, and environmental uses of such metabolically active biological materials.

The general applications of these composite biological devices are: high throughput automated drug screening/drug discovery; as composite biochemical catalysts for the manufacture of drugs, fine chemicals, and food ingredients; as implantable "tissue-like" structures in mammals, birds, or fish; as composite environmental sensors to detect the presence of environmental toxins; as bioelectronic devices to store and transmit information; as inexpensive analytical sensors for clinical, occupational, or environmental monitoring; and as efficient biocatalysts for municipal and industrial waste treatment.

A particularly useful application of this invention is for screening. This includes automated analysis of the integral biological materials (e.g., cells as the "targets") for sensitivity (killing, for example, by antibiotics, antiviral compounds, antitumor agents), bioactivity, pathogenicity, virulence, and resistance to chemical and physical challenges. These composite biological devices can also be used as sensitive indicators of gene expression from the integral biological material(s) in response to chemical or physical challenges and in the presence of other biological materials (such as cell—cell or cell-tissue interactions). These novel devices are also useful as indicators of the metabolic response of the integral biological material (e.g., measuring the waste products of cellular metabolism), growth, viability (e.g., the capability for DNA synthesis), and the ability to be stimulated/respond as the biological materials would in vivo.

Preferably, the devices are inexpensive and disposable. They can be made of both porous and nonporous materials, preferably latex polymers. They include a biostructure, which can include one or more layers of polymeric material. These layers can be continuous or discontinuous and pattern coated, thereby forming patches or reactive zones. At least a portion of the biostructure includes biological material (i.e., biomaterial). Preferably, at least a portion of the biostructure includes a nonporous latex-derived material. The biostructure can optionally be disposed on a substrate, which for certain embodiments is porous. The biostructure is preferably very thin. Preferably, it is no greater than about 500 microns thick, more preferably, no greater than about 100 microns thick, and most preferably no greater than about 10 microns thick. More preferably, the entire device, biostructure and optional substrate on which the biostructure is disposed is no greater than about 500 microns thick.

A preferred embodiment of these composite materials is for the determination of the presence of a metal in a sample. Advantageously, the devices can also quantitatively measure the amount of a metal in a sample.

Metals that can be detected, typically individually detected, and preferably quantitatively measured, include inorganic or organic forms of a variety of metals that can be toxic to humans and other species. These include, for example, mercury (typically, in the form of $Hg^{2+}$ or monomethyl mercury), arsenic (typically in the form of arsenate $AsO_4^{3-}$ or arsenite $AsO_2^-$), cadmium (typically in the form of $Cd^{2+}$), antimony (typically in the form of antimonite $SbO_2^-$), bismuth (typically in the form of $Bi^{3+}$), and copper (typically in the form of $Cu^{2+}$).

Other components (e.g., analytes in a sample of interest) that can be detected and/or quantitatively measured using the devices of the present invention include organic compounds that can be toxic to human, avian, plant, fish, insect, or other species. These include, for example, insecticides, herbicides, polycyclics, nerve gas agents, mutagens, carcinogens, antibiotics, products of combustion (e.g., tobacco smoke, coal combustion, liquid fuel combustion). Such compounds include hydrocarbons (e.g., xylene, toluene, naphthalene), halogenated hydrocarbons (e.g., trichloroethylene, carbon tetrachloride, chloroform), formaldehyde, ketones, hydrazines, and the like.

The devices can be used to determine the constituents of liquid samples such as oil, water, as well as biological fluids such as blood, urine, saliva, tears, extracts of biological tissue, for example. The liquid samples can be held by an absorbent pad, such as one made of cellulose or sponge. Alternatively and significantly, the devices can be used on solid (or semi-solid) samples such as biological tissue (e.g., from seafood, particularly fish, clams, crabs, oysters, for example) as well as sludge and soil. The devices can also be used on gaseous samples such as air.

Preferably, and significantly, the devices of the present invention are stable such that the biological material (e.g., cells or microorganisms) remain viable. (i.e., metabolically active). By stable, it is meant that they are responsive after at least about 8 hours under ambient conditions when the biostructure is in a hydrated condition (during and/or prior to use, the cells are hydrated). More preferably, the devices are stable for at least about 6 months under ambient conditions, and most preferably, indefinitely at a temperature of less than about −10° C., when the biostructure is in a prehydrated (or nonhydrated) condition. For example, devices of the present invention have been shown to remain stable (e.g., maintained 90% of its initial metabolic activity when rehydrated) for at least about 4 months at −20° C. in a prehydrated condition. The devices of the present invention are also preferably robust such that they can be handled and transported with little or no damage. The devices can be flexible. Preferably, they include an indicator coating that does not delaminate from a supporting substrate, craze, or crack.

The devices of the present invention preferably include immobilized biological material that form an integral part of the composite device. Typically, such biological material is immobilized in a polymeric layer, which can be in the form of a coating, and is preferably supported on a substrate (typically, an inert substrate that does not interact or interfere with the function of the device), although a support substrate is not required. This coating with at least one biological material therein is referred to as a "biological material-containing layer" or "biomaterial-containing layer." As used herein, a layer can be continuous or discontinuous. A variety of such layers can be combined to form a variety of structures within the device, such as channels, wells, etc.

Preferably, the devices include a multi-layered construction, which is referred to herein as a 3-dimensional microstructure. A polymeric layer that includes the immobilized biological material is typically supported on a substrate (preferably, an inert substrate). This layer forms a microporous matrix that entraps (typically, permanently entraps) whole living cells (and even microorganisms) as an integral element of the device, typically without adhering to them. The biological material can be present in the device in multiple layers if desired. Optionally, and preferably, the construction includes at least one interlayer or overlayer (i.e., sealing or sealant layer) of a polymer that does not include biological material. An overlayer can help prevent the biological material from leaving the first polymeric layer upon rehydration of the biological material with water or a water-based solution. Other layers, which may form channels, wells, or other structures in an array, are possible as well. Typically, these structures are formed by nonporous material, preferably, nonporous latex-derived polymers. Thus, as used herein, a composite device can include one or more biological material-containing polymeric layers and one or more polymeric layers that do not include biological material that can be interspersed between the biological material-containing layers or as overlayers.

In certain embodiments, the biostructures preferably include no greater than about 75% by volume of biological material, and more preferably, no greater than about 50% by volume of biological material. Cells immobilized in biostructures according to the present invention typically maintain at least about 80% of the original culturability, and preferably have rehydrated culturability that is similar or higher than that of suspended cells when compared over 15 days.

The polymeric layers of the device can be porous or nonporous. Preferably, if they contain biological material, they are porous, and if they do not, they are less porous, and even nonporous. For certain embodiments, the biostructure includes at least two different porous polymers of different pore sizes.

The porosity of a latex polymeric layer results from the fluid-filled spaces that remain between the polymer particles after polymer particle coalescence. Low porosity or nonporous latex layers are typically formed by latices with very rapid and complete polymer particle coalescence. Examples of these latices include latex paints. Such nonporous polymers can be pattern coated to form nonporous channels, reservoirs, and wells, for example.

The porosity of latex polymer layers can be controlled by a variety of methods that arrest polymer particle coalescence. Some degree of polymer coalescence or "welding" is typically required for film formation and to immobilize the biological material. Various methods exist to arrest or control the degree of polymer particle coalescence to obtain optimal porosity. For example, the degree of polymer particle coalescence can be altered by the presence of carbohydrates, or surface active agents, or by polymer particle composition, film formation temperature, and/or drying conditions.

Latex porosity is commonly measured by monitoring the rate of diffusion of a nonbinding, easily detected, low molecular mass molecule through a latex film using a diffusion apparatus. These indicator molecules rapidly diffuse through (from one side to the other) a highly porous latex film. They diffuse slowly through low porosity films.

Each layer, which may be continuous or discontinuous, may contain one or more polymer. Each polymer used is preferably derived from a latex (e.g., water delivered polymer particles), whether it be naturally occurring or synthetic. Other non-latex-derived polymers can also be used if desired. The polymer particles may be monodispersed (all of similar size), polydispersed (broad polymer particle distribution), or specific combinations thereof. The polymers can include, for example, acrylate polymers, vinyl acetate polymers, styrene polymers, butadiene polymers, carboxylate polymers, and blends or copolymers thereof. As used herein a copolymer is a polymer of two or more different types of polymers (including copolymers, terpolymers, tetrapolymers, etc.). The polymers may or may not be cross-linked. Suitable polymers are commercially available from Rohm and Haas of Philadelphia, Pa., Dupont of Wilmington, Del., H.B. Fuller Co. of Minneapolis, Minn., and GenCorp. of Magadore, Ohio, for example. Preferably, the polymeric material used for immobilizing (i.e., entrapping) biological material includes an acrylic/vinyl acetate copolymer. Preferably, the polymeric material used as an intervening or overlayer includes an acrylic/vinyl acetate copolymer.

The polymeric layers (both biological material-containing layer(s) and intervening or overlayer(s) that do not include biological material) can also include additives for various purposes, such as absorbing undesirable material, preventing microbial contamination, and increasing sensitivity. Such additives include, for example, a salt, a pigment, an adsorbent, a liquid crystal, a porosity modifier, a chelating agent, a nutrient, a surfactant, a dye, a photoreactive compound, an antibiotic, an antimicrobial, a bacteriostatic compound, an enzyme, an osmoprotectant, a biopolymer, a metals, a chemical catalyst, or a combination thereof.

Examples of such additives include, but are not limited to: salts such as NaCl, NiCl, $K_2HPO_4$, $KH_2PO_4$, calcium, magnesium, sodium and potassium carbonates; porosity modifiers such as glycerol, glucose, and sucrose; adsorbents such as $CaCO_3$, $CaSO_4$, $MgSO_4$; nutrients such as amino acids (e.g., cysteine) and carbohydrates; pigments such as $TiO_2$; dyes such as X-gal (5-bromo-4-chloro-3 indolyl-β-D-galactoside), blue dextran, and Resazurin (7-hydroxy-3H-phenoxazin-3-one-10-oxide; chelating agents such as EDTA and ammonium pyrrolidine dithiocarbamate (APDC); surfactants such as FLUORAD FC 430 (3M Co., St. Paul, Minn.); liquid crystals such as p-methoxy benzyliden-p'-n-butoxyaniline (MBBA); enzymes such as peroxidase; photoreactive compounds such as silver halides; bacteriostatic compounds such as NaF; antibiotics such as kanamycin or ampicillin; antimicrobial agents such 1,2-benzisothiazolin-3-one (ICI biocides, Wilmington, Del.); osmoprotectants such as sucrose or trehalose or glycerol; biopolymers such as gelatin; metals; and chemical catalysts. Preferably, the biomaterial-containing layer(s) include glycerol. Preferably, the other polymeric layer(s) include glycerol, bacteriostatic compounds, antibiotics, antimicrobial agents, and/or carbohydrates.

The polymeric layers (both biological material-containing layer(s) and intervening or overlayer(s) that do not include biological material) can also include physical components that can function as detectors or transmitters. These can include wires, optical fibers, electronic components such as chips, etc. These may or may not be in direct contact with the biological material, although preferably, a transmitter is adjacent to or in direct physical contact with the biological material.

Preferably, the biological material includes one or more species of prokaryotic, eukaryotic, or archean organisms as homogeneous cell populations, mixtures of microorganisms, consortia, mixed-cultures, or unspeciated naturally occurring microbial populations with a defined characteristic. The biological material can include mammalian cells, blood cells, bacterial cells, avian cells, plant cells, insect cells, spores (e.g., *Bacillus subtilis*), phages (e.g., lambda bacteriophage), viruses (e.g., HIV, HTLV), etc. The biological material can be in the form of cell clumps or cell mats (i.e., a number of different cells living together in some sort of structure), for example. Examples of suitable cells include bacterial cells such as *E. coli, Bacillus*, and *Streptomyces, Thermotoga*, archean cells such as *Pyrococcus*, eukaryotic cells such as yeast and *Penicillium*, as well as plant cells. For certain preferred embodiments, the biological material includes bacterial, yeast, or fungal cells, which may optionally be recombinant.

The biological material is preferably genetically engineered to produce a response, such as a mechanical or chemical response, and thereby emit a signal that can be detected. They are also preferably optimized for desiccation tolerance. Examples of suitable responses include, but are not limited to; emission of light (e.g., luminescence or fluorescence); production of an enzyme, metabolite, or other detectable chemical; evolution of heat; a change in $H^+$ or $OH^-$ concentration; a change in thermal or electrical conductivity; a change in pressure; production of oxygen, a change in a reactive radical concentration; or a change in tensile or compressive stress. Such response is typically produced upon contact with an analyte in a sample being analyzed. For example, a response occurs upon contact with a metal being detected. Significantly, many of these responses can be measured such that the material being detected can be quantitatively measured. Such responses can be transmitted to a detector, optionally with the aid of a transmitter. The detector and optional transmitter may be part of the device, either forming a part of the biostructure or incorporated into a substrate on which the biostructure is disposed.

Preferably, the biological material is recombinant *E. coli*, *Bacillus*, or *Streptomyces* cells that include a metal resistant promoter, such as a mercury resistant promoter, and a reporter gene encoding a protein such as, for example, luciferase, protease, β-galactosidase, alkaline phosphotase, or green fluorescent protein. Preferably, the biological material includes a bioluminescent operator/promoter mer-lux plasmid, although other operator/promoter constructs can be used including ars-lux, smt-lux, and cad-lux.

Several mer-lux plasmid constructs are known. The constructs made by Selifonova et al. (*Appl. Environ. Microbiol.*, 59, 3083–3090, (1993)) are particularly useful in that each construct has been tested extensively for mercury sensitivity in suspended cultures under different conditions. These plasmids are pRB28, pOS14, and pOS15. They all code for luciferase activity (luxCDBE) but differ in the subset of mer genes fused to the lux gene. pRB28 contains merR (the mer repressor gene) and a truncated merT (one of the mer transporter genes). A second construct, pOS14, contains merR and the complete set of mercury transport genes merT, merP, and merC. The third construct, pOS15, contains merRTPC, the reductase gene (merA) and a second regulatory gene (merD). Induction of the mer operon by inorganic mercury results in the production of luciferase which can be assayed by the ATP-dependent emission of photons.

Preferably, the biostructure (preferably, in the form of a 3-dimensional microstructure or array) is supported on a substrate. The substrate can interface with the biostructure if it includes a detector or transmitter. Typically, however, the substrate is an inert substrate, which is one that does not take part in or interfere in the function of the device. The substrate can be in a wide variety of forms, such as a film, wire, membrane, filament, foam, etc., including combinations of such materials. It can be transparent or translucent. It can be made of a wide variety of materials, which may be porous or nonporous, synthetic or naturally occurring, including metals, glasses, ceramics, and organic polymers (e.g., nylon, polyester, polycarbonate, and polyacetate). Examples of substrates include paper, woven or nonwoven fiber mats, plastic sheets, etc. The substrate can include electronic components, such as electrodes, semiconductor devices.

In particularly preferred embodiments, the substrate enables detection and/or measurement of the metal by monitoring the signal produced upon the biological material responding to contact with the metal (e.g., luminescence). For such preferred embodiments, the supporting substrate can be a photosensitive film or a light-sensitive electronic chip, for example. Alternatively, the substrate can merely support or protect the biological material and not take part in the detection of the metal. For such embodiments, the supporting substrate can be a solid, light impenetrable backing, for example. In such embodiments in which the supporting substrate does not detect the signal emitted by the biological material, the biological material would need to be brought into close proximity to a detector. Such a detector could be, for example, a photosensitive film that does not have a cell-containing indicator coating thereon, a scintillation counter, or light meter. This occurs in the embodiments described below with respect to FIGS. 3, 8, and 10.

The methods of detection include various detection mechanisms. For example, such methods can involve detecting light fluorescence as from expression of Lux, a fluorescent protein, detecting a hydrolytic enzyme activity such as protease activity, detecting the production of a metabolite, detecting the evolution of heat, detecting a change in $H^+$, $OH^-$, or reactive radical concentration change, detecting the evolution of a gas such as carbon dioxide, detecting the utilization or depletion of a substrate such as glucose, and/or detecting a change of color. A preferred method is the expression of Lux.

The polymeric layers, with or without biological material incorporated therein, may be formed, for example, by a wide variety of methods, including, for example, draw down coating, slot coating, die coating, spin coating, gravure coating, or piezo-electric or acoustic printing (e.g., inkjet or laser jet printing having piezo-electric or acoustic pumps). Typically, the biological material-containing layer(s) are dried prior to the overlayer(s) being applied. A typical coating process of a polymeric layer on a substrate can be carried out at temperatures varying from about 4° C. to about 95° C. The coating method preferably provides good control over biological material distribution, and coating thickness which leads to easily standardized responses or measurements. Alternatively, however, the layers can be simultaneously coated or coated sequentially without intervening drying steps, if so desired. The layers may also be pattern coated.

Pattern coating of a rapidly coalescing latex facilitates formation of device microstructures consisting of, for example, nonporous latex walls, dams, or barriers to restrict gas and liquid flow or diffusion. This pattern coating method can be repeated multiple times to deposit nonporous latex polymer to predetermined thickness or height. Using this method, device structures such as channels, reservoirs, microwells, etc., can be made. This same method can also be used to generate complex three-dimensional (3-D) interconnected arrays of channels linking reactive zones, which are regions of the pattern coating containing integral biological material (preferably, substantially permanently entrapped biomaterial). One example is shown in FIG. 17.

A particularly preferred method of forming the biostructures of the devices of the present invention is through the use of piezo-electric or acoustic printing (e.g., ink jet or laser jet printing). This method, compared to rod, bar, or slot coating methods can immobilize biomaterial in high resolution multilayer microstructures, which can be in the form of a patch, of such high density (e.g., number per unit area) and high specific activity (e.g., number of cells per microstructure) that remarkable gains can be realized in biosensor sensitivity, biocatalyst volumetric activity, screening sensitivity, and productivity. This technique can eject or jet biological material in pico-liter sized droplets. Polymeric material can be combined with the biological material or applied separately by using two fusing streams. Millions of single droplets can be deposited in ultra-high densities (e.g., greater than about 1000 dots per inch (dpi)) at very high rates.

A suitable printing apparatus may include ink-jet heads containing several rows of nozzles (e.g., 32 nozzles in 4 rows), each nozzle acting as a separate pump and each row feeding from a separate reservoir, which allows mixing of at least 4 different liquid streams as they are deposited resulting in creation of one or multiple gradients during deposition. A multi-channel wash and refill position may be incorporated into the apparatus so that individual rows of nozzles can be washed and refilled any number of times with new media as a part of the printing operation. Current piezo-electric pumps can deposit 6 pL ($6 \times 10^{-12}$ L) in 45 micron droplets. The corresponding density of individual immobilized cell drops one drop diameter apart is $12.3 \times 10^3$ drops/cm$^2$ or $7.4 \times 10^6$ drops on an 8.5×11 inch sheet.

Using such printing techniques, a wide variety of reaction zones can be created, each with its own micro-environment. For example, regions of various antibiotic concentrations can be generated by depositing different amounts of liquid from nozzles connected to separate reservoirs on a print head. Alternatively, a large number of plant pathogens can be printed and immobilized in a polymer matrix in an array. Thus, a single plant leaf can be exposed to a large number of plant pathogens simultaneously.

The devices may optionally include a removable film (a "top" film) that protects the biomaterial-containing layers. This top or protective film is typically a layer of foil, although it could be a layer of cellulose acetate, or a wide variety of other synthetic or natural materials. The devices may also optionally include a removable film (a "bottom" or protective film) that protects the supporting substrate, such as a light-sensitive electronic chip.

Various embodiments of the devices of the present invention are described by reference to the figures. Many of these devices are described with respect to the detection of mercury (whether it be in the form of inorganic mercury such as $Hg^{2+}$ or organic mercury such as monomethyl mercury), although other metals or organic materials could be detected. Also, many of these devices are described with respect to the detection of mercury in fish tissue or fluids, although other samples could be tested. Furthermore, many of the embodiments include cells that emit light upon exposure to mercury. Again, this is only for illustration purposes as other types of cells or other biological materials can be used and the devices modified accordingly, which would be readily apparent to one of skill in the art upon reading the teachings herein.

Figure 1B:
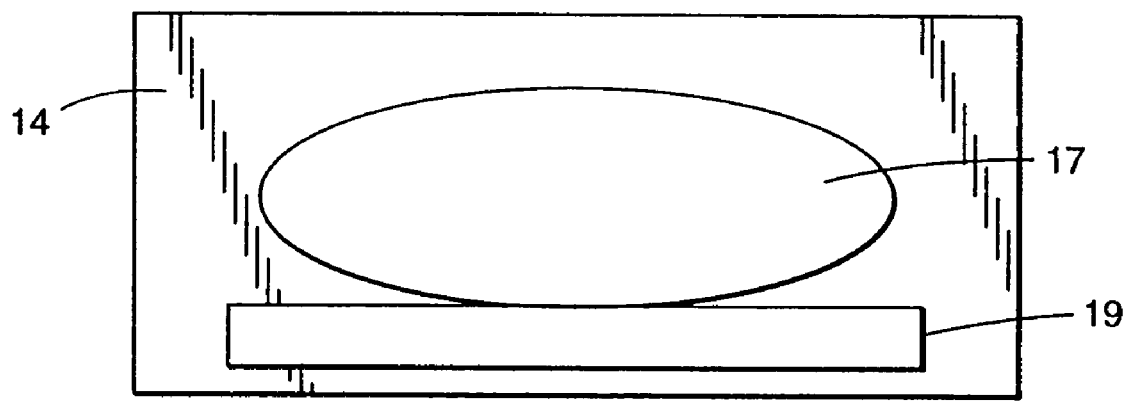
FIG. 1B is a bottom view of the device of FIG. 1A showing the photosensitive film.

FIG. 1A shows a basic structure for a device according to the present invention. The device 10 includes a biostructure 12, which is in the form of a biomaterial-containing layer. This includes immobilized cells and is also referred to herein as a cell-containing indicator coating. The biostructure 12 is disposed on a photosensitive film 14 (the supporting substrate). The device also includes removable protective films 16 (first or top film) and 18 (second or bottom film), which may be made of foil and may or may not include pull tabs (which is shown for film 16). FIG. 1B is a bottom view of the photosensitive film 14 (such as a commercially available sheet of POLAROID film) after the film 18 is removed showing a photosensitive area 17, which displays a response to mercury. Also shown is a built-in photodensity measuring device 19, which is used as a comparator. For example, the photodensity measuring device 19 can be a strip of material, such as paper or plastic, having printed thereon an image with increasing black density graduated to correspond to the level of mercury detected. The photodensity measuring device 19 also could be a mercury-containing compound spread on the surface at an increasing concentration. In this way, the device would include an internal standard for quantifying the level of mercury. Thus, in both cases the strip would be labeled with the mercury concentration. In use, the top film 16 is removed to expose the immobilized cells to the sample of interest. The immobilized cells, sample of interest, and nutrients (such as glucose in the presence of a buffer, for example) are incubated (for example, under ambient conditions for at least about 15 minutes). The bottom film 18 is then removed and the level of mercury (which may be in the form of inorganic mercury and/or monomethyl mercury) is determined by viewing the photosensitive area 17 and comparing it to the photodensity measuring device 19.

FIG. 2A shows an alternative construction for a device 20 in which a biostructure 22 (in the form of a biomaterial-containing layer having immobilized cells therein) is disposed on a light-sensitive electronic chip 24. The device also includes removable protective film 26, which may or may not include a pull tab (which is shown for film 26). FIG. 2B is a bottom view of the electronic chip 24, which may be reusable, and has an electrical connection 25. In use, the film 26 is removed to expose the immobilized cells to the sample of interest. The immobilized cells, sample of interest, and nutrients are incubated as described above. The level of mercury is measured with a voltmeter (not shown). The light generated by the cells is measured by the voltage generated by the light sensitive chip.

FIG. 3 shows an alternative structure for a device 30 in which a biostructure 32 (in the form of a biomaterial-containing lazer having immobilized cells therein) is disposed on a substrate 34 that does not detect the signal (e.g., light, heat, etc.) produced by the cells. The substrate shown is not light transmissive, although this is not a necessary requirement. The device also includes removable protective film 36, which may or may not include a pull tab (which is shown for film 36). In use, the film 36 is removed to expose the immobilized cells to the sample of interest. The immobilized cells, sample of interest, and nutrients are incubated as described above. The light generated by the cells is measured with an external meter, such as a scintillation counter or light meter. The mercury is correlated to the light level. Hand-held or laboratory meters are available.

FIG. 4 shows a device 40 that can penetrate into a sample of interest, such as fish tissue, through the scales, skin, and into the tissue. The penetration device 40 includes the construction shown in FIG. 1, which includes a biostructure 42 disposed on a photosensitive film 44 (or alternatively, it could include the constructions shown in FIG. 2 or 3). The device also includes removable bottom film 48 (and a top film, which is not shown). In use, a cut is made in the fish, the top film (not shown) that protects the biostructure 42 is removed, device 40 is inserted into the cut and placed there for a predetermined length of time to sorb the mercury. The device is removed and incubated with nutrients as described above. The level of mercury is then measured by evaluating the photosensitive film 44.

Figure 5:
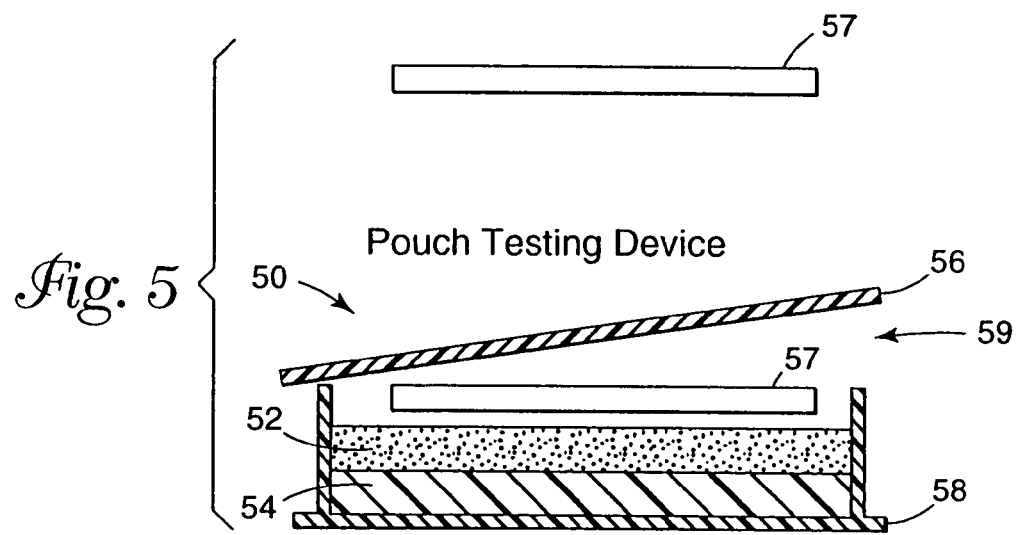
FIG. 5 is a cross-sectional schematic of an alternative embodiment of a device according to the present invention that includes a cavity for placement of a solid sample, such as fish tissue.

FIG. 5 shows yet another construction for a device 50 according to the present invention. The device 50 is in the form of a container, such as a pouch. It includes a biostructure 52 (having immobilized cells therein) disposed on a supporting substrate 54, such as a photosensitive film or a light-sensitive electronic chip, for example. The device also includes removable protective films 56 and 58. The top film 56 is not in direct contact with the biostructure 52; rather, it is spaced above it, thereby forming a cavity 59 for placement of a sample 57, such as a slice of fish tissue. In use, the film 56 is removed and the sample 57 is placed in the cavity 59 in direct contact with the biostructure 52. The immobilized cells, sample, and nutrients are incubated as described above. The film 58 is then removed and the level of mercury is measured using the substrate 54.

Figure 6:
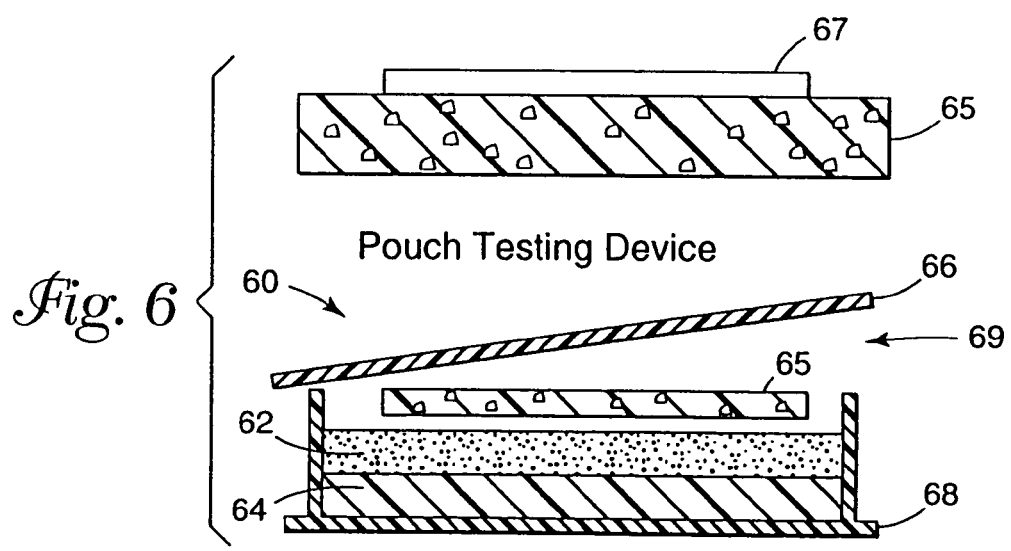
FIG. 6 is a cross-sectional schematic of an alternative embodiment of a device according to the present invention that includes a cavity for placement of a solid sample containing a fluid, such as an absorbent pad containing fluids from fish tissue.

FIG. 6 shows a very similar device to that shown in FIG. 5. In this embodiment, the sample of interest, such as fish tissue need not be placed in the cavity; rather an absorbent pad 65, which can be made of cellulose or sponge, for example, containing fluids from the fish tissue can be used. The device 60 includes a biostructure 62 disposed on support 64, which can be a photosensitive film or a light-sensitive electronic chip, for example. The device also includes removable protective films 66 and 68. As in the device shown in FIG. 5, the top film 66 is not in direct contact with the biostructure 62; rather, it is spaced above it, thereby forming a cavity 69 for placement of an absorbent pad 65. In use, the film 66 is removed and the absorbent pad 65, which had been in contact with a slice of fish 67 to absorb fluids from the fish tissue, is placed in the cavity 69 in direct contact with the biostructure 62. The immobilized cells, absorbent pad, and nutrients are incubated as described above. The film 68 is then removed and the level of mercury is measured using the support 64.

Figure 7B:
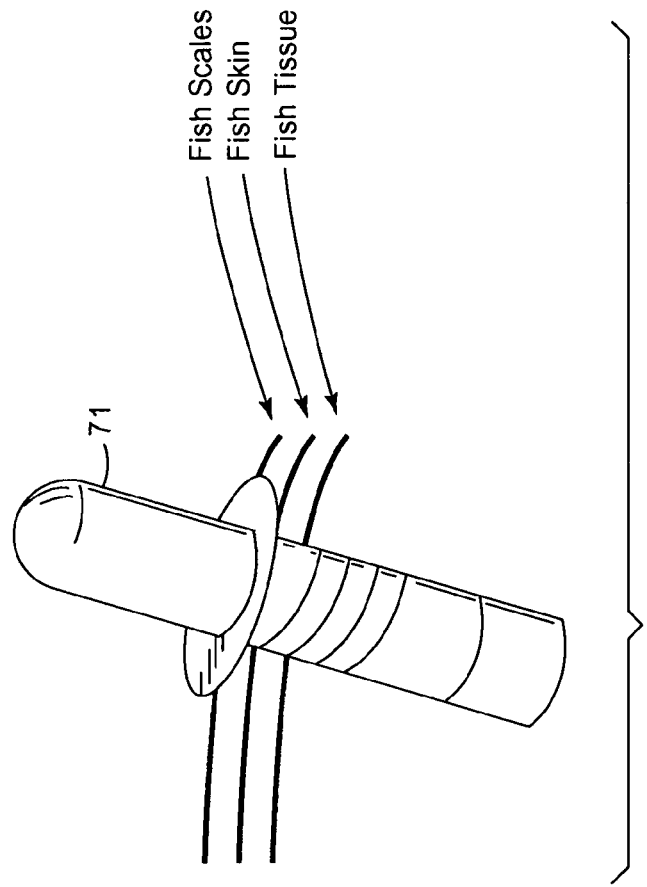
FIG. 7B shows the device of FIG. 7A penetrating fish scales, skin, and tissue.
Figure 7A:
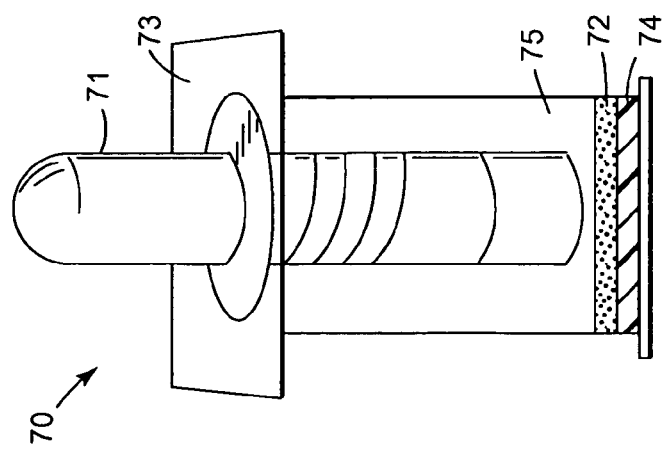
FIG. 7A is a schematic of an alternative embodiment of a device according to the present invention that can be used to penetrate through fish scales, skin, and tissue and remove a core sample of tissue.

FIG. 7A shows a device 70 that includes the construction shown in FIG. 1 (or alternatively, it could include the constructions shown in FIG. 2 or 3), that includes a coring device 71 that is inserted into a container 73. The container 73 includes a reservoir 75, which is filled with nutrients and buffer. The bottom of the container 73 (or optionally the sides of the container) includes a biostructure 72 disposed on a photosensitive film 74. As shown in FIG. 7B, the coring device 71 is designed to penetrate fish scales, skin, and tissue, as described above for FIG. 4. It is used to remove a core sample of fish tissue and deliver this core sample to the reservoir 75 in container 73. Both the coring device 71 and the container 73 can have threads such that the coring device 71 is screwed into the container, although this is not a requirement. The mercury from the tissue sample migrates to the immobilized mercury sensitive cells located in the biostructure 72 in the bottom (or sides) of the container 73. The reservoir 75 includes nutrients in a buffer for incubation of the cells. The light generated by the cells is detected by a photosensitive film 74 (e.g., POLAROID film) attached to the bottom (or sides) of the nutrient reservoir 75.

Figure 8B:
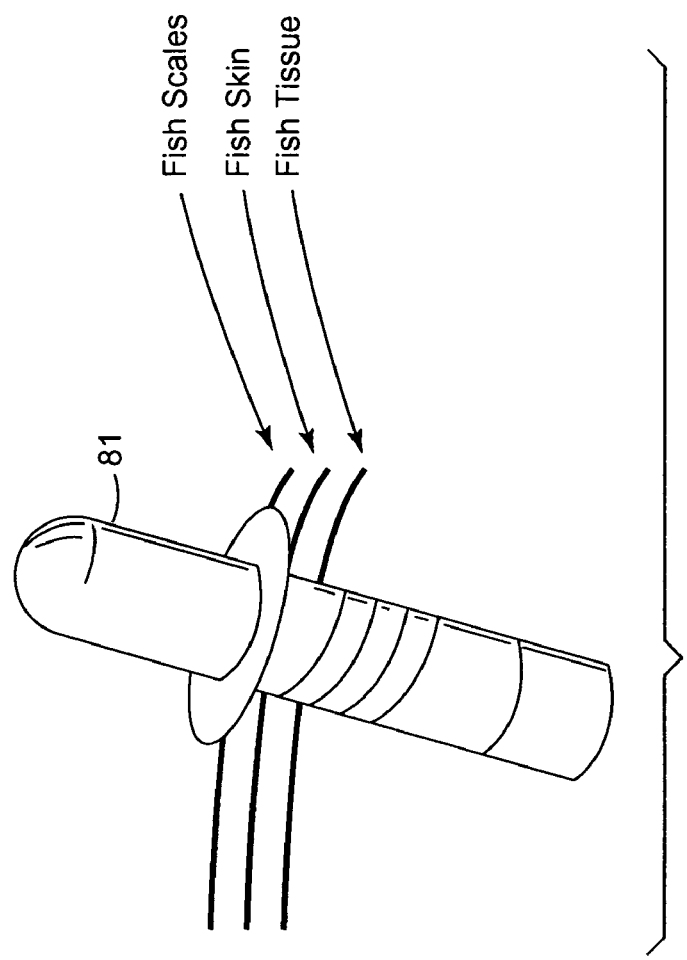
FIG. 8B shows the device of FIG. 7A penetrating fish scales, skin, and tissue.
Figure 8A:
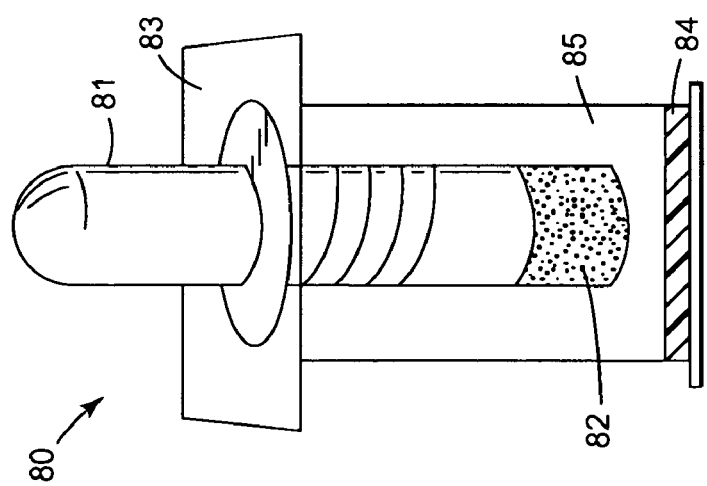
FIG. 8A is a schematic of an alternative embodiment of a device according to the present invention that can be used to penetrate through fish scales, skin, and tissue.

FIG. 8A shows a device similar to that shown in FIG. 7, except that the coring device 81 includes a biostructure 82 (having immobilized cells therein) directly on the coring device 81. Also, the coring device 81 does not need to be hollow. Thus, it does not necessarily remove a core tissue sample from a fish as described with respect to FIG. 7. In this embodiment and as shown in FIG. 8B, the immobilized cells located in the tip of the coring device 81 are exposed to the fish tissue while it is inserted in the fish tissue. After exposure to the fish tissue, the coring device 81 is inserted into the reservoir-85 of container 83 where the cells are incubated in buffer and nutrients. The light generated by the cells is detected by a photosensitive film 84 (e.g., POLAROID film) attached to the bottom (could also be the sides) of the nutrient reservoir 85.

FIG. 9 shows a device that allows for a sample to be drawn into a reservoir, such as into a syringe. In device 90 there is a construction as described above for FIG. 1. In FIG. 9A, a side view shows a cross-section of the device 90 that includes a biostructure 92 coated on a photosensitive film 94. The device also includes removable protective film 98. The device 90 also includes a syringe needle 91, a reservoir 93, and a bulb 95, which can be used to draw up a liquid sample into the reservoir 93. The biostructure 92 is positioned inside the reservoir 93 with photosensitive film 94 and protective film 98 forming an external wall. FIG. 9B is a bottom view of the photosensitive film 94 (e.g., POLAROID film) after the film 98 is removed showing a photosensitive area 97, which displays a response to mercury. Also shown is a built-in photodensity measuring device 99 as described above with respect to FIG. 1. In use, a liquid sample is drawn into the reservoir 93, where it comes in contact with the immobilized cells of the biostructure 92. Nutrients are added and the cells and sample are incubated. The film 98 is then removed and the level of mercury is measured by evaluating the photosensitive area 97 as it compares to the photodensity measuring device 99.

FIG. 10 discloses a device that includes a biostructure in the form of a cell-containing indicator coating coated on a fiber 100, composed of, for example, polyester, nylon, cellulose acetate, or an optical fiber. This fiber can be an optical fiber, for example. As shown in FIG. 10A, the coated fiber 100 has an end-stop 101 and a penetrating end 103. The device is shown penetrating through a fish tail. Once a sufficient amount of time has lapsed for the immobilized cells of the cell-containing indicator to be in contact with the fish tissue, the coated fiber 100 is removed. As shown in FIG. 10B, the coated fiber 100 is then placed in contact with a photosensitive film 104, which can be in a pouch or container, for example, having nutrients and buffer therein. After a sufficient incubation period, the mercury can be qualitatively detected by viewing a photographic image 105 of the thread on the photosensitive film 104.

FIG. 11A shows a cross-section of a coated fiber 100, as shown in FIG. 10. The coated fiber 100 includes a monofilament 106 coated with a biostructure 102. The biostructure 102 includes a cell-containing polymeric layer 107 and a polymeric overlayer 108. FIG. 11B shows a cross-section of a coated fiber 110 that includes a multiple filament thread 116 with a biostructure 112. The biostructure 112 includes a cell-containing polymeric layer 117 and a polymeric overlayer 118. The coated fiber 110 may also include a polymeric precoat layer 119 between the multiple filament thread 116 and the cell-containing polymeric layer 107.

Figure 12:
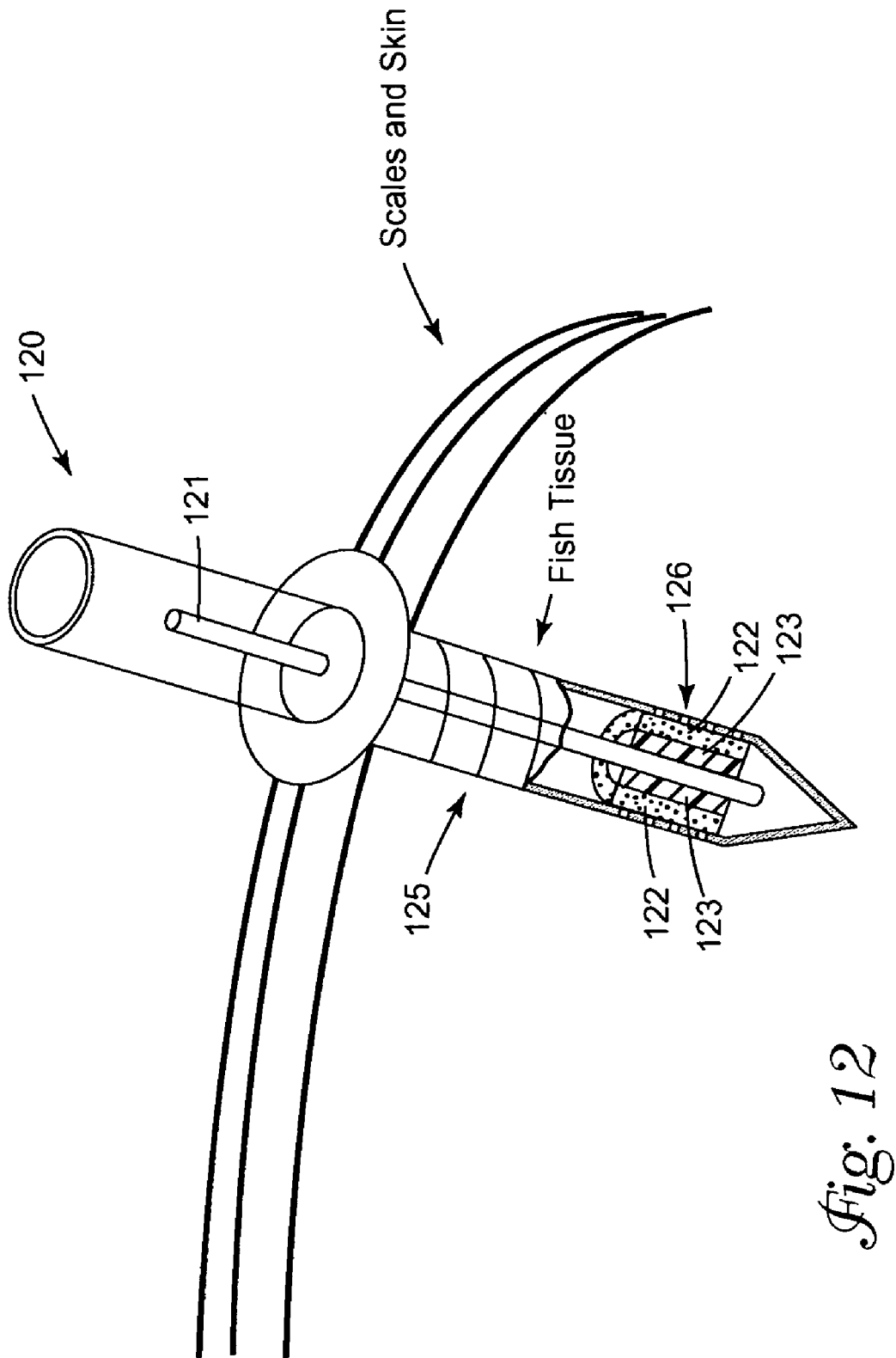
FIG. 12 is a schematic of an alternative embodiment of a device according to the present invention that includes a pop-up indicator and a protein or lipid-based glue and immobilized cells containing a protease reporter gene.

FIG. 12 shows a device 120 in which cells are used that contain a plasmid with a mercury resistance promoter that activates a gene to produce a secreted protease or lipase. The cells are included in a biostructure 122. A pop-up indicator rod 121 is initially held in place by a protein or lipid based glue 123. The pop-up indicator rod 121 may be used either qualitatively or quantitatively, if it includes an indicator scale (not shown). The device also includes a spring 125 under tension that is attached to the pop-up indicator rod 121. In use, the device 120 is inserted into fish tissue. When mercury is detected by the cells in the biostructure 122 as it diffuses through a perforated housing 126 of device 120, the resulting protease or lipase degrades the glue 122 and releases the rod 121. As a result of the tension placed on the rod 121 by the spring 125, the rod moves up. By the design of the rod, the glue, and the glue holder the device could be made to be quantitative. Alternately, the pop-up indicator rod 121 could be attached to a piston to measure the production of a gas. In that case the cells would contain the genes needed to produce high levels of gas when activated. In an alternative embodiment, the biostructure could include a protein or lipid based glue in place of, or in addition to, the polymer used to make the biostructure.

Figure 13:
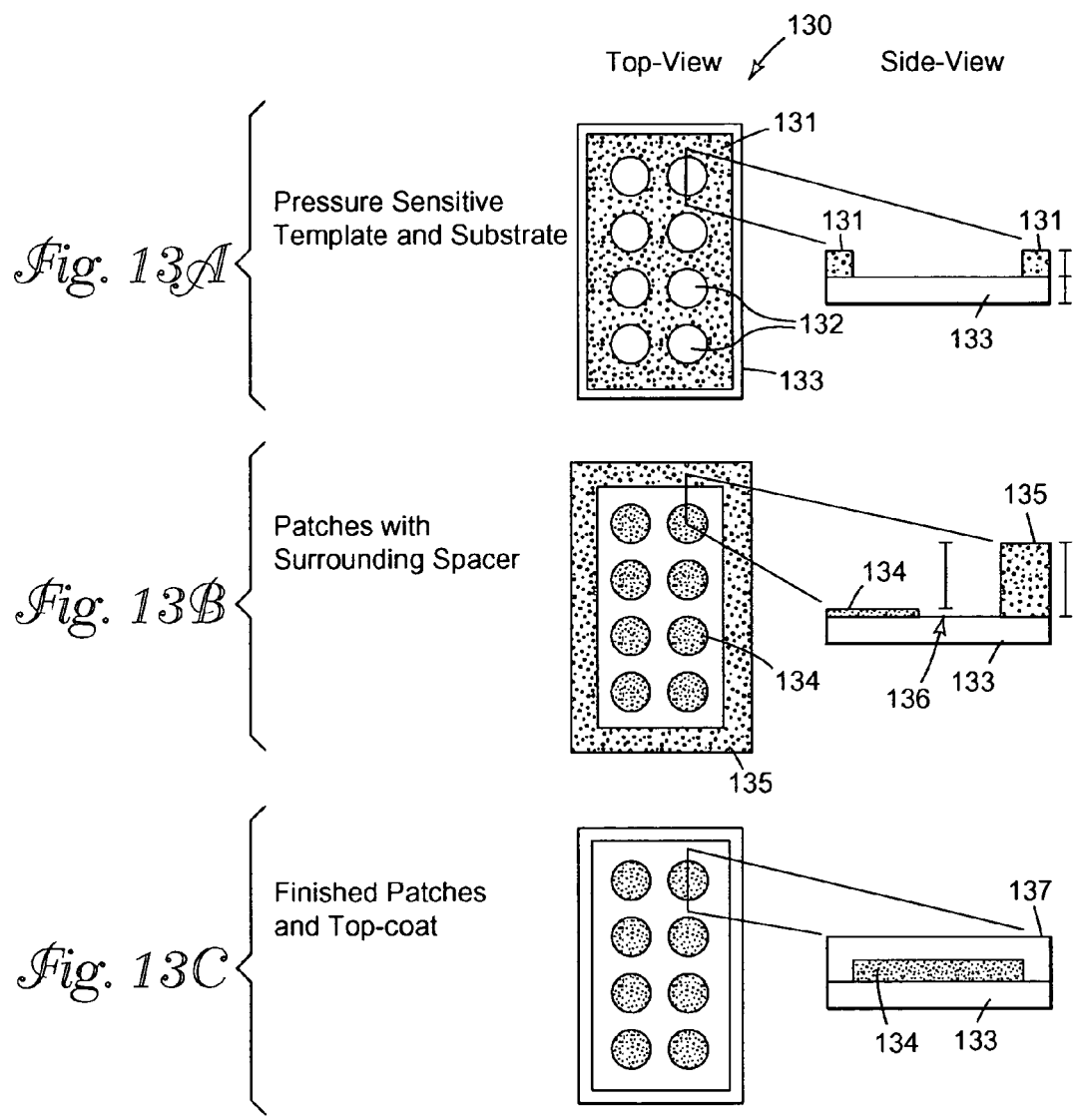
FIG. 13 is a schematic of preferred template assemblies before cell-coating, after cell coating, and after top-coating. A: Top-view and side-view of template assembly; B: cell-coat patches with surrounding spacer; C: finished top-coated patches.

FIG. 13 is a schematic of a preferred template assembly used to make patches of cell-containing indicator coatings with a top-coating. FIG. 13A is a top-view and side-view of template assembly 130. The template assembly 130 includes a template 131, which can be made of a variety of materials, such as paper, and includes holes 132 punched therein. The template 131 (e.g., 42.4 microns thick) is disposed on a supporting substrate 133 (e.g., 48 microns thick). FIG. 13B is a top view and side view of cell-coat patches 134 (e.g., 30 microns thick) with surrounding spacer 135 (e.g., 155 microns thick) and a gap 136 (to be filled by a top coat) therebetween. FIG. 13C is a top view and side view of finished top-coated patches that include cell-coated patches 134 on a substrate 133 and a top or sealant coating 137 disposed on the cell-coated patches 134 and substrate 133 in the gaps 136.

Figure 14:
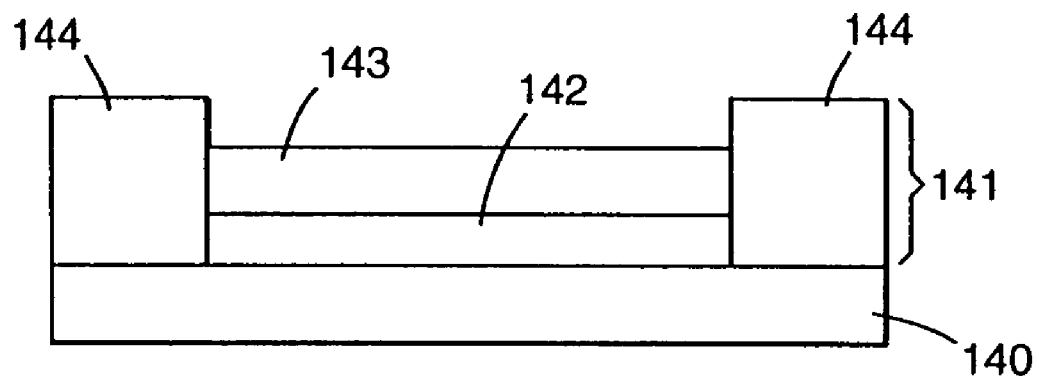
FIG. 14 is a schematic of a latex biosensor patch containing a viable E. coli coating, a porous sealant coating, and a nonporous wall coating.
Figure 15:
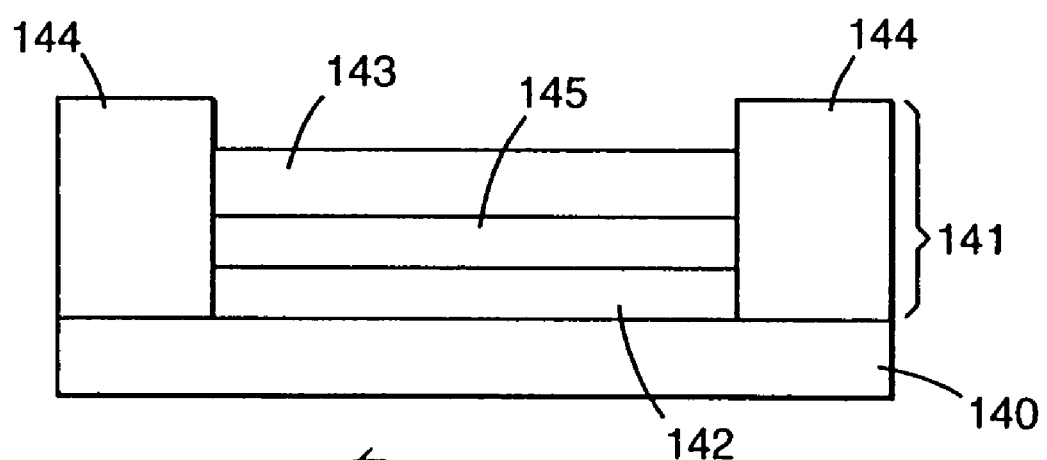
FIG. 15 is a schematic of a latex biosensor patch containing a viable E. coli coating, a porous sealant coating, a mercury adsorbent (such as APDC) layer coating, and a nonporous wall coating.

Another embodiment of the present invention is shown in FIG. 14. In this embodiment, a polyester substrate 140 is coated with a biostructure 141. The biostructure 141 includes a porous latex layer 142 containing viable E. coli cells, a porous latex sealant coating 143, and a discontinuous nonporous latex layer 144 which form walls. FIG. 15 includes these layers plus a porous latex layer 145 with a mercury absorbant material disposed between the porous sealant coating 143 and porous latex layer 142 containing a viable E. coli cells.

Figure 16:
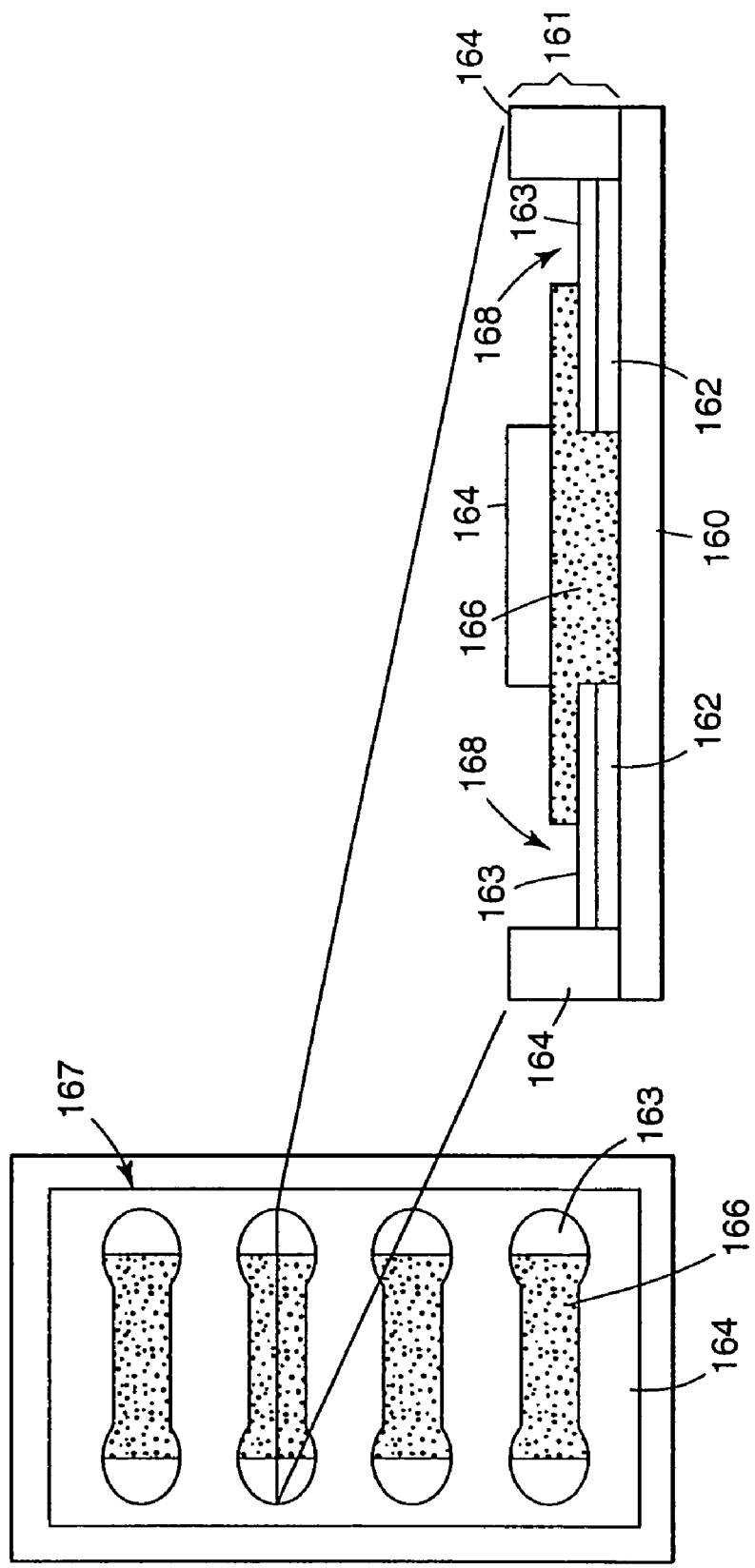
FIG. 16 is a schematic of a latex biosensor patch containing a viable E. coli coating, a porous sealant coating, a porous channel coating, and a nonporous wall and sealant coating.
Figure 17A:
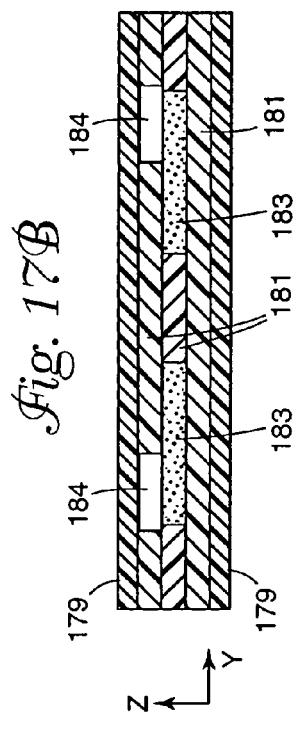
FIG. 17 is a schematic of a layered porous array of microwells with bidirectional channels.
Figure 17B:
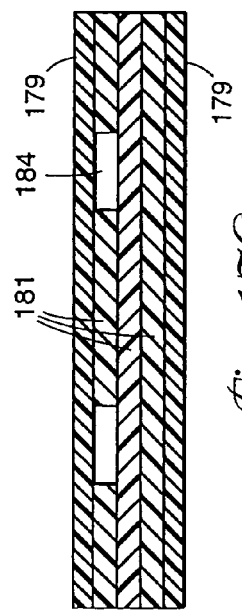
Figure 17C:
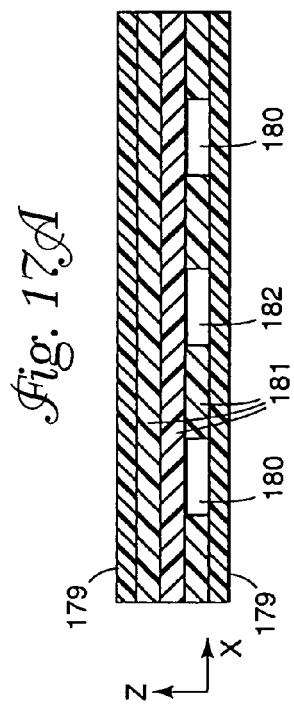
Figure 17D:
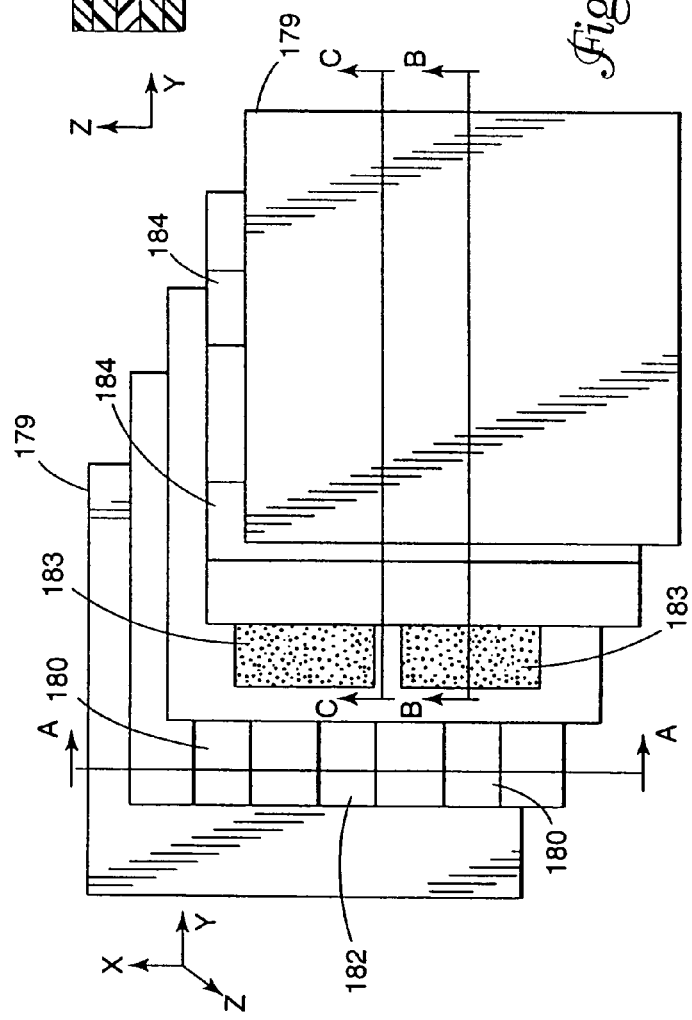
Figure 18A:
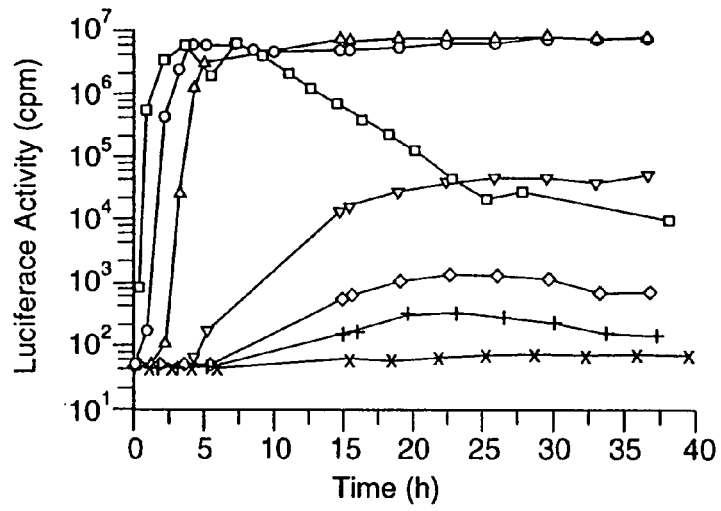
FIG. 18 provides a chart of luciferase activity of latex film-immobilized E. coli HB101 containing mer-lux constructs after induction by $HgCl_2$ in pyruvate buffer. (A) pRB28. (B) pOS14, (C) pOS15. Symbols: (□) 10,000 nM $HgCl_2$, (○) 1,000 nM $HgCl_2$, (Δ) 100 nM $HgCl_2$, (∇) 0 nM $HgCl_2$, (◊) 1 nM $HgCl_2$, (+) 0.1 nM $HgCl_2$, and (x) 0 nM $HgCl_2$.
Figure 18B:
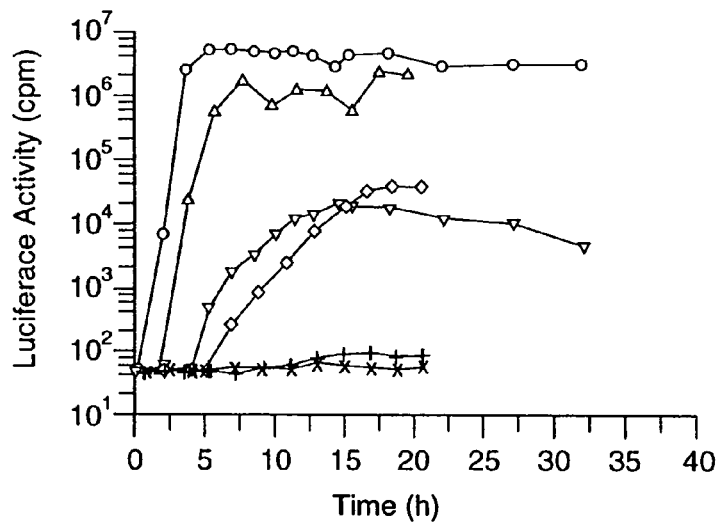
Figure 18C:
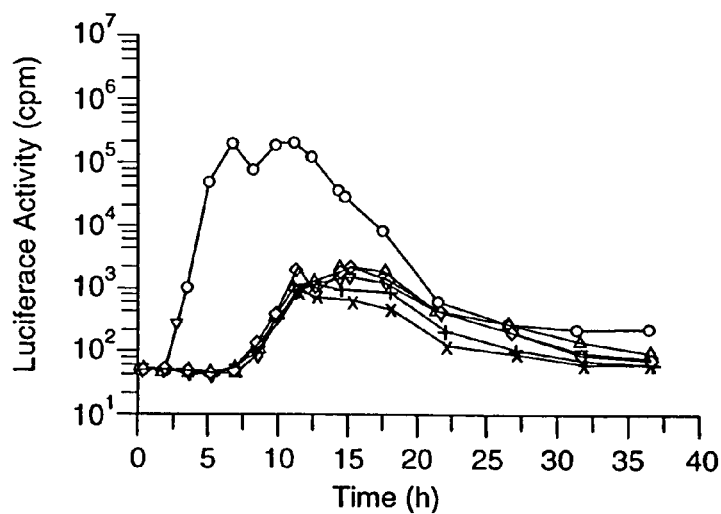
Figure 19A:
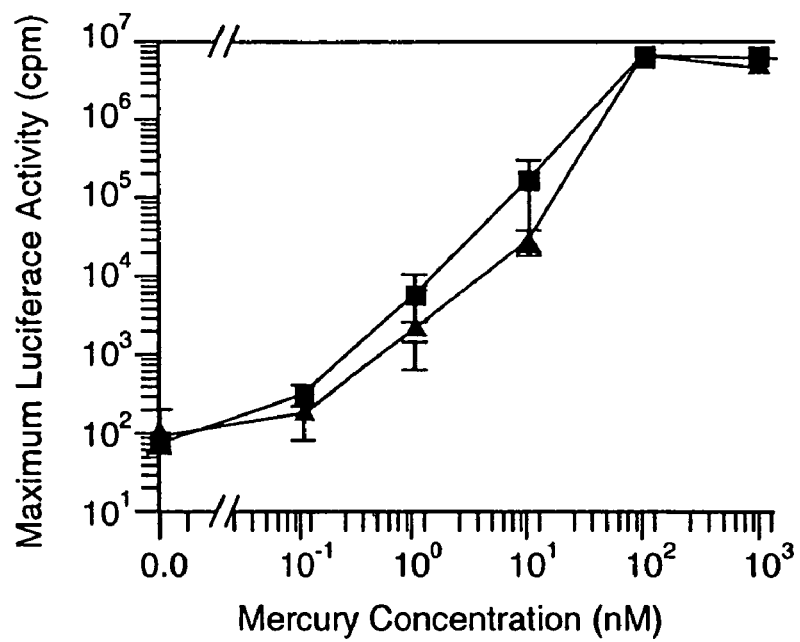
FIG. 19 provides a chart of the effect of storage on latex-immobilized E. coli HB101 (pRB28). Maximum luciferase activity was plotted as a function of mercury concentration. (A) at −20° C. for 3 month. Symbols: (■) immobilized cells freshly made, (▲) immobilized cells stored at −20° C. for 3 months in glycerol: PBS buffer (50:50 w/w). (B) at ambient temperature dry 14 days. Symbols: (■) immobilized cells freshly made, (▼) immobilized cells stored ambient temperature for 14 days dry.
Figure 19B:
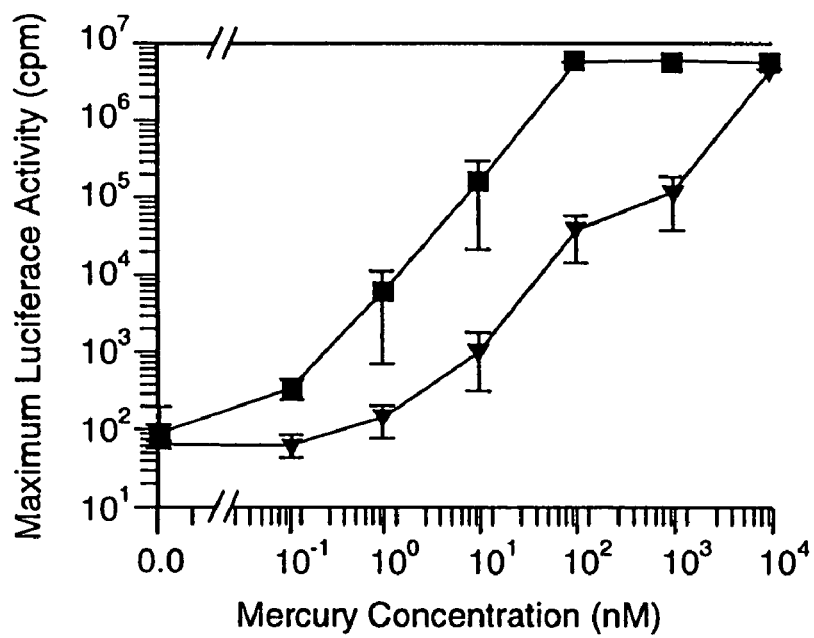

Yet another embodiment of the present invention is shown in FIG. 16. This includes a polyester substrate 160 on which is disposed a biostructure 161. The biostructure 161 includes a discontinuous porous latex layer 162 containing viable E. coli cells, a discontinuous porous latex sealant coating 163, and a discontinuous nonporous latex layer 164. These layers form a porous channel 166 between two wells 168. The outline of the nonporous latex template that forms the wells 168 and channel 166 is represented by 167.

FIG. 17 represents a layered porous array of microwells with bidirectional channels for delivery of drug screening candidates. The device is shown with four reaction zones. As shown in FIG. 17A (a cross-section taken along line A) the device includes impermeable top and bottom layers 179, y-direction feed channels 180, nonporous filler layers 181, waste channel 182 shown in the y-direction, but could be in the x-direction also. A cross-section of the device taken along line B, shows a reaction zone of immobilized biological particles 183, and a x-direction feed channel 184. A cross-section of the device taken along line C again shows the x-direction feed channels 184.

Devices containing 3-dimensional microstructures as shown in FIG. 17 can be used for screening new drug candidates. For example, for cells that produce a candidate that needs to be screened against a large number of targets, a microstructure could be designed in which a matrix of candidate-producing cells are immobilized on top of a polymer layer containing a matrix of target molecules.

Objects and advantages of this invention are further illustrated by the following examples, but the particular materials and amounts thereof recited in these examples, as well as other conditions and details, should not be construed to unduly limit this invention.

EXAMPLES

Method for Preparing Mercury Biosensor Films of *Escherichia coli*

Bacterial Strains and Media. The methods procedures and techniques are substantially those found in well known molecular cloning and genetics guides such as Maniatis et al., *Molecular Cloning: a Laboratory Manual*, Cold Spring Habor, N.Y., 1982. Materials are commercially available from sources such as GIBCO/BRL, Gathersburg, Md., or Promega, Madison, Wis. *E. coli* HB101 containing pRB28, pOS14, or pOS15 are in the public but could be constructed through these cloning methods as described by Selifonova et al., *Appl. Environ. Microbiol.*, 59, 3083–3090, (1993)).

Coating Materials. Harvested *Escherichia coli* HB101 cells were mixed with glycerol and acrylic/vinyl acetate copolymer latex (Rohm and Haas, Philadelphia, Pa.) in a ratio depending on the number of cells immobilized. Commonly used was 1.2 g cell paste, 0.3 ml 50% (w/w) glycerol, 1 ml latex, which were mixed together. The cell-polymer mixture was coated onto a polyester template (e.g., pressure sensitive adhesive tape) using a 26 mil wire wound rod (Mayer bar) at 4° C., as described in greater detail below. After the coated layer was dry, the template was removed, and a second layer of latex (overlayer) was coated on top. The topcoat layer was dried at 4° C., and the assembly was cured at 37° C. for 30 minutes or shorter. Individual patches were excised and rehydrated in buffer (5 mM pyruvate, NaK-phosphate buffer pH 6.8 [34 mM sodium phosphate; 33 mM potassium phosphate, pH adjusted to 6.8] and 0.091 mM $(NH_4)_2SO_4$). The preparation of the template and coating procedure is described in detail below and with reference to FIG. 13.

Coating Method. A punch was used to create circular holes in a pressure sensitive tape such as that obtained from Minnesota Mining & Manufacturing Company, St. Paul, Minn., under the trade designation SM 7830 to form a template. The template was rolled onto a substrate of similar length and width. This creates uniform circular wells of a desired diameter and depth (12.7 mm diameter and 42.6 μm well depth was commonly used), as shown in FIG. 13A. A pool of cell-polymer mix was delivered at the top of the template in a line spanning the width of the patch area. A 26 mil wire diameter Mayer rod was placed above and then drawn through the coating liquid and across the wells formed by the template. The cell-coat was dried until no moisture was visible. At 4° C. and 70% relative humidity, drying took 2 hours. The template was then peeled off. As shown in FIG. 13B, a spacer consisting of a pressure sensitive tape was placed around the newly formed cell-coat patches to prevent the Mayer rod from touching during coating. Commonly used spacer thickness was 155 μm. The spacer was laid down on all four sides of the substrate containing the cell patches to contain the top-coating liquid during drying. A pool of sealant liquid (latex with 5% glycerol) was delivered in line spanning the width of the area enclosed by the spacer and coated with a 26 mil wire diameter Mayer rod. After the top-coat had dried, the spacer was removed, leaving the construction shown in FIG. 13C. The top-coat was dried at 4° C. and 70% relative humidity for 2.5 hours until it took on a transparent and matte appearance.

Detection of Mercury,

FIG. 18

Section A. Patches of immobilized *E. coli* HB101 harboring the pRB28 mer-lux constructs were analyzed individually in 20 ml scintillation vials in a liquid scintillation counter, (single photon counting mode, 1 minute counting time, Beckman, LS 7000, Columbia, Md.) for luciferase activity after exposure (the patches were submerged in the liquid containing the mercury) to $HgCl_2$ concentrations from 0.1 nM to 10,000 nM. Luciferase activity induced by 0.1, 1, or 10 nM HgCl$_2$ was not apparent during the first 5 hours of induction but increased substantially during the next 15 hours after which time the activity continued to increase or remained constant until 37 hours. E. coli HB101 (pRB28) exposed to higher levels of Hg(II) had significantly different kinetics of luciferase induction. At 100, 1,000 or 10,000 nM HgCl$_2$, the luciferase activity reached maximum detection levels (limited by the scintillation counter to 6×10$^6$ count of single photons per minute) within the first 5 hours of induction.

Section B. Patches of immobilized E. coli HB101 harboring the pOS14 mer-lux constructs were analyzed individually for luciferase activity after exposure to HgCl$_2$ concentrations from 0.1 nM to 10,000 nM, at 0.1 nM HgCl$_2$. Light induction was not significant compared to the control. Hg(II) concentrations at 1 nM and 10 nM induced luciferase activity after a 4–5 hour lag, and luciferase activity increased during the next 10 hours of the assay. At 100, 1,000 and 10,000 nM HgCl$_2$, luciferase activity was evident after 2 hours of incubation and reached the maximum detectable (6×10$^6$ count of single photons per minute) after 5–8 hours.

Section C. Patches of immobilized E. coli HB101 harboring the pOS15 mer-lux constructs were analyzed individually for luciferase activity after exposure to HgCl$_2$ concentrations from 0.1 nM to 1,000 nM. The only concentration of Hg(II) that showed significant luciferase induction above background levels with pOS15 was 1,000 nM HgCl$_2$.

FIG. 19

Patches containing E. coli HB 1101 (pRB28) cells that were identical to those used for HgCl$_2$ induction of luciferase activity in pyruvate buffer were stored at −20° C. for 3 months or as dry (meaning nonrehydrated) for 14 days. Samples were then either thawed or rehydrated in pyruvate phosphate buffer mentioned above and exposed to HgCl$_2$. The induced maximum luciferase activity was compared to freshly prepared immobilized cell patches. Freezing the patches did not significantly affect luciferase induction. Maximum sensitivity for frozen stored patches was 0.1 nM HgCl$_2$ equal to that of non-stored patches. Also the range (0.1 to 100 nM HgCl$_2$) in which a detectable change in signal was observed was unchanged. Storage 14 days dry decreased the maximum luciferase activity observed between 100 nM and 0.1 nM HgCl$_2$. The maximum sensitivity decreased from 0.1 nM to 1 nM HgCl$_2$. The range in which there was a detectable change in signal was expanded to the range 1 nM to 10,000 nM HgCl$_2$.

Method for Preparing 3D Microstructures

Bacterial Strains, Chemicals, Media, and Growth Conditions. Bacterial strain: E. coli HB101 containing pRB28. Growth medium: Luria-Bertani (LB) medium (10 g/l tryptone (Difco), 5 g/l yeast extract (Difco), 5 g/l NaCl [analytical grade], pH 7.2) containing 50 µg/ml kanamycin (Sigma Chemical Company, St. Louis, Mo.) at 30° C. E. coli was grown overnight in 300 ml growth medium in 2 liter Erlenmeyer flask at approximately 150 rpm in a Labline shaker (model 3525CC) and were harvested by centrifugation for 15 minutes at 2800×g. The cell pellet was washed in pyruvate buffer (5 mM pyruvate, NaK-phosphate buffer pH 6.8 [34 mM sodium phosphate; 33 mM potassium phosphate, pH 6.8] and 0.091 mM (NH$_4$)$_2$SO$_4$) before repelleting at 2800×g for 15 min.

Latex Materials. Porous sealant coating: Rovace SF091 containing 0.4 volume sucrose per volume dry latex polymer. Nonporous coating material: Rovace SF091 with no additives. Porous channel material Rhopaque HP 1055 containing 1.5 ml/ml JP1225 latex. Absorbant layer material (absorbent for Hg$^{2+}$ ions) Rovace SF091 containing 0.4 volume sucrose per volume dry latex polymer and ammonium pyrrolidine dithiocarbamate (APDC) 0.05 g/L. Cell coat material: 1.2 g of washed wet cell pellet gently resuspended in 0.3 ml 50% (v/v) glycerol in water with 1 mL Rovace SF091 added immediately prior to coating.

Template, Mask, Spacer and Coating Materials. Coatings were cast on clear 2 mil polyester (3M, St. Paul, Minn.). Templates and masks were made from pressure sensitive clear vinyl (42.6 µm) (Con-Tact, Stamford, Conn.) and spacers from Marker tape (155 µm) (TimeMed, Chatsworth, Calif.).

Preparing Templates and Masks. A template is a pressure sensitive tape with sections cut out where the coating liquid is to contact the underlying coating or substrate. A template can be applied on top of a clean substrate or on an already coated substrate. Masks are single pieces of pressure sensitive tape placed on top of the substrate or on coatings. After application of one or more layers on top of a template or mask each template or mask can be removed to expose the layer(s) beneath. Each template or mask was generated by manually punching with a ½ inch diameter punch (O'Brien Consolidated Industries, Lewiston, Me.) or cutting with a razor blade. Templates were generated by taping 5 pieces of pressure sensitive tape (clear vinyl) to the backside of a template figure and each section was cut through the 5 template pieces simultaneously on a poly-vinyl chloride board. The individual template sheets were separated and cleaned with KIMWIPEs to remove dust. Templates with nicks or tears were discarded since these would prevent them from separating from the substrate without tearing. Templates were applied onto the substrate or coating by rolling them onto it with a hard rubber roller (Orcon Corporation, Union City, Calif.). This method created uniform sections for patches or channels with a depth of 42.6 µm.

Coating of Latex Polymers. All coating layers were coated using wire wound rods (Mayer bars) with a wire diameter of 26 mil (R. D. Specialities, Webster, N.Y.). Coatings were created on a constant pressure draw down coating apparatus (R. D. Specialities, Webster, N.Y.) with a 31 cm×46 cm vacuum table (Paul N. Gardner Company, Inc, Pompona Beach Fla.) on top and dried at 18° C. for 30 minutes.

Detection of Luciferase Activity in Immobilized E. coli HB101. Patches with latex immobilized E. coli HB101 cells were exposed to HgCl$_2$ by soaking them in 10 ml of pyruvate buffer (induction buffer) containing 100 nM or 0 nM HgCl$_2$ in sterile glass scintillation vials. Hg(II) concentrations were confirmed by cold vapour atomic fluorescence spectroscopy CVAFS (Brooks Rand Model III, Seattle, Wash.). Immobilized cell samples were incubated in triplicate at ambient temperature, and luciferase activity was detected as counts per minute of ATP-dependent photon emission in a liquid scintillation counter (Beckman, LS 7000, Columbia, Md.).

Latex Biosensor Patch Shown in FIG. 14. This device was created by coating a cell-latex mixture onto an 8 hole ½ inch diameter template on a polyester substrate. The coating was then dried. A sealant coating was coated on top of the cell coating with the template still in place. Following drying of the sealant coating the template was removed leaving two layered patches of approximately 60 micron thickness on the substrate. A mask consisting of ½ inch circles were applied to each patch. A spacer was laid around the patches on each side to prevent contact between the Mayer rod and the masks during coating. A nonporous coating was subsequently coated on top of the masked patches and dried before removal of the masks. Induction at 100 nM Hg$^{2+}$ resulted in a photon emission count of 500,000 counts per minute resulting from the mercury induced expression of luciferase. Induction at 0 nM $Hg^{2+}$ resulted in less than 61 photon counts per minute.

Latex Biosensor Patch Shown in FIG. 15. This device was created by coating a cell-latex mixture onto an 8 hole ½ inch diameter template on a polyester substrate. The coating was then dried. An absorbent coating was coated on top and dried. A sealant coating was coated on top of the absorbent coating with the template still in place. Following drying of the sealant coating the template was removed leaving three layered patches of approximately 90 micron thickness on the substrate. A mask consisting of ½ inch circles were applied to each patch. Surrounding the patches on each side a spacer was laid down to prevent contact between the Mayer rod and the masks during coating. A nonporous coating was subsequently coated on top of the masked patches and dried before removal of the masks. Induction at 100 nM $Hg^{2+}$ resulted in a photon emission count of less than 1000 counts per minute resulting from the mercury induced expression of luciferase. The result demonstrated that the absorbent layer reduced the induced activity by 500 times. Induction at 0 nM $Hg^{2+}$ resulted in less than 50 photon counts per minute.

Latex Biosensor Patch Shown in FIG. 16. This device was created by coating a cell-latex mixture onto an 8 hole ½ inch diameter template on a polyester substrate. The coating was then dried. A sealant coating was coated on top of the cell coating with the template still in place. Following drying of the sealant coating the template was removed leaving two layered patches of approximately 60 micron thickness on the substrate. A second template consisting of ½ inch by 1 inch rectangular holes was applied on top of the patches so that ¼ inch of the patches were covered and so that the open area connected to opposing patches. A porous channel layer was coated on top of the second template and dried. The second template was subsequently removed. A mask consisting of ½ inch circles was applied to each patch. A spacer was laid around the patches on each side to prevent contact between the Mayer rod and the masks during coating. A nonporous coating was subsequently coated on top of the masked patches and the porous channel layer and dried before removal of the masks. Each patch with its channel was subsequently excised so that each patch had a ½ inch channel attached. 5 mm of the channel end was placed in induction buffer, leaving the circular part with cells out of direct contact with the induction buffer. Induction at 100 nM $Hg^{2+}$ resulted in a photon emission count of more than 50,000 counts per minute resulting from the mercury induced expression of luciferase. Induction at 0 nM $Hg^{2+}$ resulted in less than 110 photon counts per minute.

Latex Biosensor Patch as in FIG. 14 Created on a Piezo-Electric Ink-Jet Printer. This sample was created by coating a cell-latex mixture and nonporous latex concurrently using an ink-jet printer (Canon PJ-1080a) with a piezo-electric print head. The cell latex mixture was loaded into the yellow color ink reservoir, the nonporous latex was loaded into the black color ink reservoir, and the porous latex mixture was loaded into the blue color ink reservoir. Patches were coated by printing 4 times on top of the same area a cell-latex center surrounded by a nonporous latex layer. Each coating step was followed by a drying step prior to coating again. Total patch thickness was approximately 3 microns after 4 coatings. Following the last printing and drying step a nonporous sealant coating was printed on top of the entire coated area. Four different patch sizes were made. Patch sizes were 9 mm×9 mm, 4.5 mm×4.5 mm, 1.28 mm×0.96 mm, and 0.64 mm×0.64 mm. Induction at 100 nM $Hg^{2+}$ resulted in a photon emission count above noninduced patches of the same size of 99,980 cpm for 9×9 mm patches, 767 cpm for 4.5×4.5 mm patches, 11 cpm for 1.28×0.96 mm patches, and 3 cpm for 0.64×0.64 mm patches.

The complete disclosures of the patents, patent documents, and publications cited herein are incorporated by reference in their entirety as if each were individually incorporated. Various modifications and alterations to this invention will become apparent to those skilled in the art without departing from the scope and spirit of this invention. It should be understood that this invention is not intended to be unduly limited by the illustrative embodiments and examples set forth herein and that such examples and embodiments are presented by way of example only with the scope of the invention intended to be limited only by the claims set forth herein as follows.

What is claimed is:

1. A composite biological device comprising a biostructure comprising at least one biological material as an integral imbedded component within the biostructure,
    wherein at least a portion of the biostructure comprises a nonporous latex-derived material and at least a portion of the biostructure comprises a porous latex-derived material having the at least one biological material imbedded therein,
    wherein the biological material is a cell or microbe and metabolically active or becomes metabolically active upon hydration, and
    further wherein the biostructure is obtainable by gravure coating, piezo-electric printing, or acoustic printing.

2. The composite device of claim 1 wherein the biological material comprises a prokaryote, a eukaryote, an archean organism, or a combination thereof.

3. The composite device of claim 1 wherein the biological material comprises a mammalian cell, a blood cell, an avian cell, a plant cell, an insect cell, a bacteriophage, a spore, a virus, or a combination thereof.

4. The composite device of claim 1 wherein the biological material comprises a recombinant bacterial, yeast, or fungal cell.

5. The composite device of claim 4 wherein the recombinant cell is desiccation tolerant.

6. The composite device of claim 1 wherein the biostructure further comprises at least one additive selected from the group of a salt, a pigment, an adsorbent, a liquid crystal, a porosity modifier, a chelating agent, a nutrient, a surfactant, a dye, a photoreactive compound, an antibiotic, an antimicrobial, a bacteriostatic compound, an enzyme, an osmoprotectant, a biopolymer, a metal, a chemical catalyst, and a combination thereof.

7. The composite device of claim 1
    wherein the biostructure further comprises a transmitter incorporated therein.

8. A method of determining the presence of an analyte in a sample, the method comprises contacting the sample with the device of claim 7 wherein, upon contact with the analyte, the biological material produces a response and emits a signal; and detecting the signal.

9. The composite device of claim 1 wherein the biostructure further comprises a detector incorporated therein.

10. The composite device of claim 9 wherein the detector senses a response emitted from the biological material when in contact with an analyte.

11. A method of determining the presence of an analyte in a sample, the method comprises contacting the sample with the device of claim 9 wherein, upon contact with the analyte, the biological material produces a response and emits a signal; and detecting the signal.

12. The composite device of claim 1 wherein the latex-derived material is cross-linked.

13. A method of determining the presence of an analyte in a sample, the method comprises contacting the sample with the device of claim 12 wherein, upon contact with the analyte, the biological material produces a response and emits a signal; and detecting the signal.

14. The composite device of claim 1 wherein the biostructure is non-hydrated and the biological material becomes metabolically active upon hydration.

15. The composite device of claim 1 wherein the porous latex-derived material comprises a mixture of latices.

16. The composite device of claim 1 wherein the biostructure is supported on a substrate distinct from the nonporous latex-derived material.

17. The composite device of claim 16, wherein the substrate comprises a membrane, a filament, a wire, a film, a foam, a metal, a glass, a ceramic, an organic polymer, an electrode, a semiconductor device, or combinations thereof.

18. The composite device of claim 16 wherein the substrate comprises a metal or a polymeric material.

19. The composite device of claim 16 wherein the substrate is an electronic device.

20. The composite device of claim 1 wherein the biostructure comprises wires or electrodes.

21. A method of determining the presence of an analyte in a sample, the method comprises contacting the sample with the device of claim 20 wherein, upon contact with the analyte, the biological material produces a response and emits a signal; and detecting the signal.

22. The composite device of claim 1 wherein the biostructure is no greater than about 500 microns thick.

23. The composite device of claim 1 wherein the entire device is no greater than about 500 microns thick.

24. A method of determining the presence of an analyte in a sample, the method comprises contacting the sample with the device of claim 1, wherein, upon contact with the analyte, the biological material produces a response and emits a signal; and detecting the signal.

25. The composite device of claim 1 wherein the biostructure comprises a porous sealant layer that does not include biological material.

26. A composite biological device comprising a layered biostructure comprising at least one biological material as an integral component within the biostructure,
wherein the biostructure comprises:
at least one layer comprising a porous latex-derived material having the at least one biological material imbedded therein, and
at least one layer comprising a nonporous latex-derived material,
wherein the biological material is a cell or microbe and metabolically active or becomes metabolically active upon hydration, and
further wherein the biostructure is obtainable by gravure coating, piezo-electric printing, or acoustic printing.

27. A method of determining the presence of an analyte in a sample, the method comprises contacting the sample with the device of claim 26 wherein, upon contact with the analyte, the biological material produces a response and emits a signal; and detecting the signal.

28. A composite biological device comprising a biostructure comprising at least one biological material as an integral component within the biostructure,
wherein at least a portion of the biostructure comprises a nonporous latex-derived material and at least a portion of the biostructure comprises a porous latex-derived material having the at least one biological material imbedded therein,
wherein the biological material is a cell or microbe and metabolically active or becomes metabolically active upon hydration,
wherein the nonporous material defines at least one channel or at least one well, and
further wherein the biostructure is obtainable by gravure coating, piezo-electric printing, or acoustic printing.

29. A method of determining the presence of an analyte in a sample, the method comprises contacting the sample with the device of claim 28, wherein, upon contact with the analyte, the biological material produces a response and emits a signal; and detecting the signal.

30. A composite biological device comprising a biostructure comprising at least one biological material as an integral component within the biostructure,
wherein at least a portion of the biostructure comprises a nonporous latex-derived material and at least a portion of the biostructure comprises a porous latex-derived material having the at least one biological material imbedded therein,
wherein the biological material is a cell or microbe and metabolically active or becomes metabolically active upon hydration,
wherein the biostructure comprises no greater than about 75% by volume biological material, and
further wherein the biostructure is obtainable by gravure coating, piezo-electric printing, or acoustic printing.

31. The composite device of claim 30 wherein the biostructure comprises no greater than about 50% by volume biological material.

32. A method of determining the presence of an analyte in a sample, the method comprises contacting the sample with the device of claim 30, wherein, upon contact with the analyte, the biological material produces a response and emits a signal, and detecting the signal.

33. A composite biological device comprising a three-dimensional biostructure comprising at least one biological material as an integral, imbedded, permanently trapped, component within the biostructure,
wherein at least a portion of the biostructure comprises a nonporous latex-derived material and at least a portion of the biostructure comprises a porous latex-derived material having the at least one biological material imbedded therein,
wherein the biological material is a cell or microbe and metabolically active or becomes metabolically active upon hydration, and
further wherein the biostructure is obtainable by gravure coating, piezo-electric printing, or acoustic printing.

34. A composite biological device comprising a biostructure comprising at least one biological material as an integral imbedded component within the biostructure, at least one porosity modifier, and at least one osmoprotectant,
wherein at least a portion of the biostructure comprises a nonporous latex-derived material and at least a portion of the biostructure comprises a porous latex-derived material having the at least one biological material imbedded therein, and
further wherein the biological material is a cell or microbe and metabolically active or becomes metabolically active upon hydration.

35. The composite device of claim 34 wherein the porosity modifier is sucrose.

36. The composite device of claim 34 wherein the osmoprotectant is glycerol.

37. A method of determining the presence of an analyte in a sample, the method comprises contacting the sample with the device of claim 34 wherein, upon contact with the analyte, the biological material produces a response and emits a signal; and detecting the signal.

38. A composite biological device comprising a biostructure comprising at least one biological material as an integral imbedded component within the biostructure, wherein at least a portion of the biostructure comprises a nonporous latex-derived material and at least a portion of the biostructure comprises a porous latex-derived material having the at least one biological material imbedded therein, further wherein the biological material is a cell or microbe and metabolically active or becomes metabolically active upon hydration, and further wherein the device is stable for at least 6 months under ambient conditions.

39. A method of determining the presence of an analyte in a sample, the method comprises contacting the sample with the device of claim 38 wherein, upon contact with the analyte, the biological material produces a response and emits a signal; and detecting the signal.

* * * * *

UNITED STATES PATENT AND TRADEMARK OFFICE
CERTIFICATE OF CORRECTION

PATENT NO. : 7,132,247 B1 Page 1 of 1
APPLICATION NO. : 09/647475
DATED : November 7, 2006
INVENTOR(S) : Lyngberg et al.

It is certified that error appears in the above-identified patent and that said Letters Patent is hereby corrected as shown below:

TITLE PAGE, under "OTHER PUBLICATIONS",
insert -- "Bug Light:1998 Discover Technology Awards," Discover, 19(7):84"--

Column 20
Line 27, (Claim 1), before "metabolically active or" insert --is--

Column 21,
Line 56, (Claim 26), before "metabolically active or" insert --is--

Column 22
Line 6, (Claim 28), after "and" insert --is--
Line 27, (Claim 30), before "metabolically active or" insert --is--
Line 28, (Claim 30), after "hydration," insert --and--
Line 51, (Claim 33), before "metabolically active or" insert --is--
Line 65, (Claim 34), after "and" insert --is--

Column 24
Line 4, (Claim 24), after "and" insert --is--

Signed and Sealed this

Thirtieth Day of January, 2007

JON W. DUDAS
*Director of the United States Patent and Trademark Office*